US012565682B2

(12) United States Patent
Vodala et al.

(10) Patent No.: US 12,565,682 B2
(45) Date of Patent: Mar. 3, 2026

(54) METHODS OF TREATING CANCER

(71) Applicant: NANTCELL, INC., Culver City, CA (US)

(72) Inventors: Sadanand Vodala, Culver City, CA (US); Andrew Nguyen, Culver City, CA (US); Charles Joseph Vaske, Culver City, CA (US); Shahrooz Rabizadeh, Culver City, CA (US)

(73) Assignee: NantCell, Inc., Culver City, CA (US)

( * ) Notice: Subject to any disclaimer, the term of this patent is extended or adjusted under 35 U.S.C. 154(b) by 951 days.

(21) Appl. No.: 17/780,798

(22) PCT Filed: Nov. 25, 2020

(86) PCT No.: PCT/US2020/062334
§ 371 (c)(1),
(2) Date: May 27, 2022

(87) PCT Pub. No.: WO2021/108641
PCT Pub. Date: Jun. 3, 2021

(65) Prior Publication Data
US 2023/0028698 A1     Jan. 26, 2023

Related U.S. Application Data

(60) Provisional application No. 62/941,376, filed on Nov. 27, 2019.

(51) Int. Cl.
| | |
|---|---|
| *C12Q 1/6886* | (2018.01) |
| *A61K 31/513* | (2006.01) |
| *A61K 31/519* | (2006.01) |
| *A61K 31/675* | (2006.01) |
| *A61K 31/7056* | (2006.01) |
| *A61K 31/7068* | (2006.01) |
| *A61K 33/243* | (2019.01) |
| *A61K 35/12* | (2015.01) |
| *A61K 38/17* | (2006.01) |
| *A61K 38/20* | (2006.01) |
| *A61K 39/00* | (2006.01) |
| *A61K 39/395* | (2006.01) |
| *A61K 45/06* | (2006.01) |
| *A61K 47/64* | (2017.01) |
| *A61P 35/00* | (2006.01) |
| *A61P 37/04* | (2006.01) |

(52) U.S. Cl.
CPC .......... *C12Q 1/6886* (2013.01); *A61K 31/513* (2013.01); *A61K 31/519* (2013.01); *A61K 31/675* (2013.01); *A61K 31/7056* (2013.01); *A61K 31/7068* (2013.01); *A61K 33/243* (2019.01); *A61K 35/12* (2013.01); *A61K 38/1793* (2013.01); *A61K 38/2086* (2013.01); *A61K 39/0011* (2013.01); *A61K 39/001164*

(2018.08); *A61K 39/00117* (2018.08); *A61K 39/001182* (2018.08); *A61K 39/3955* (2013.01); *A61K 45/06* (2013.01); *A61K 47/643* (2017.08); *A61P 35/00* (2018.01); *A61P 37/04* (2018.01); *C12Q 2600/106* (2013.01); *C12Q 2600/158* (2013.01)

(58) Field of Classification Search
CPC ...................................................... A61K 35/12
See application file for complete search history.

(56) References Cited

U.S. PATENT DOCUMENTS

2016/0289760 A1* 10/2016 Suzuki .................. G16B 30/10

FOREIGN PATENT DOCUMENTS

| | | |
|---|---|---|
| EP | 2937698 | 10/2015 |
| WO | WO 2016/071890 | 5/2016 |

OTHER PUBLICATIONS

ClinicalTrials.gov. Retrieved on May 13, 2025 from the internet: https://clinicaltrials.gov/study/NCT03387085. (Year: 2025).*
Tamura et al. Oncology Letters. 2016. 11:3643-3649. (Year: 2016).*
Hazama et al. Journal of Translational Medicine. 2014. 12:108, 10 pages. (Year: 2014).*
Schrama et al. Semin Immunopathol. 2017. 39:255-268. (Year: 2017).*
McNeel. Journal for Immuno Therapy of Cancer. 2016. 4:69. (Year: 2016).*
Tanneau et al. Journal for Immuno Therapy of Cancer. 2013. 1(Suppl 1):P112. (Year: 2013).*
Hopkins et al. JCI Insight. 2018. 3(13):e122092. (Year: 2018).*
Hogan et al. Cancer Immunol Res. 2019. 7(1):77-85. (Year: 2019).*
Kansy et al. Oncoimmunology. 2018. 7(11):e1494112. (Year: 2018).*
Tamura et al., "Characterization of the T cell repertoire by deep T cell receptor sequencing in tissues and blood from patients with advanced colorectal cancer," Oncology Letters, Jan. 21, 2016, vol. 11, pp. 3643-3649.
Hogan et al., "Peripheral Blood TCR Repertoire Profiling May Facilitate Patient Stratification for Immunotherapy against Melanoma," Cancer Immunology Research, Nov. 13, 2018, vol. 7(1), pp. 77-85.

(Continued)

*Primary Examiner* — Joseph G. Dauner

(74) *Attorney, Agent, or Firm* — Sheridan Ross P.C.

(57) ABSTRACT

Multimodal cancer immunotherapy is a combination of cancer immunotherapies used to treat cancer in patients. T cell receptor diversity is used as a component of a method to treat cancer involving cancer therapy, including multimodal cancer immunotherapy.

9 Claims, 12 Drawing Sheets

Specification includes a Sequence Listing.

(56) References Cited

OTHER PUBLICATIONS

Hosoi et al., "Increased diversity with reduced 'diversity evenness' of tumor infiltrating T-cells for the successful cancer immunotherapy," Scientific Reports. Jan. 18, 2018, . Scientific Reports, vol. 8(1), Jan. 18, 2018, pp. 1-12.

Kuehm et al., "Checkpoint blockade immunotherapy enhances the frequency and effector function of murine tumor-infiltrating T cells but does not alter TCR[beta] diversity," Cancer Immunology Immunotherapy, Jul. 2019 (published online May 18, 2019), vol. 68(7), pp. 1095-1106, 17 pages.

International Search Report and Written Opinion for International (PCT) Patent Application No. PCT/US2020/062334, dated Apr. 13, 2021 11 pages.

International Preliminary Report on Patentability for International (PCT) Patent Application No. PCT/US2020/062334, dated Jun. 9, 2022 8 pages.

* cited by examiner

FIG. 2

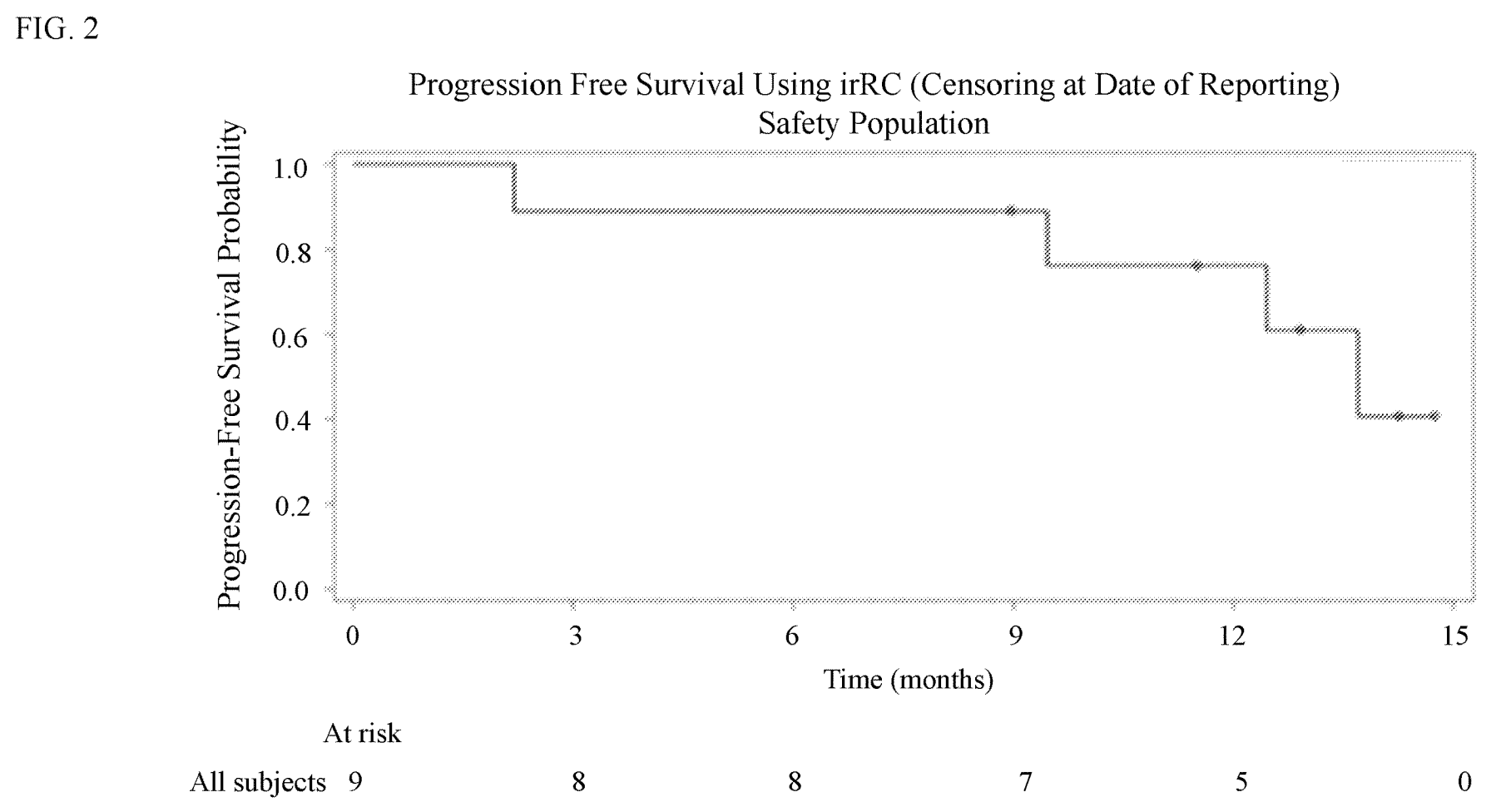

Progression Free Survival Using irRC (Censoring at Date of Reporting) Safety Population Progression-Free Survival Probability Time (months)

At risk

All subjects | 9 | 8 | 8 | 7 | 5 | 0

Subject 186 clonotypes

Total no. of CDR3 clonotypes

Left columns, of column pairs:    Right columns, of column pairs:
at least 100 reads                      at least 50 reads

FIG. 9

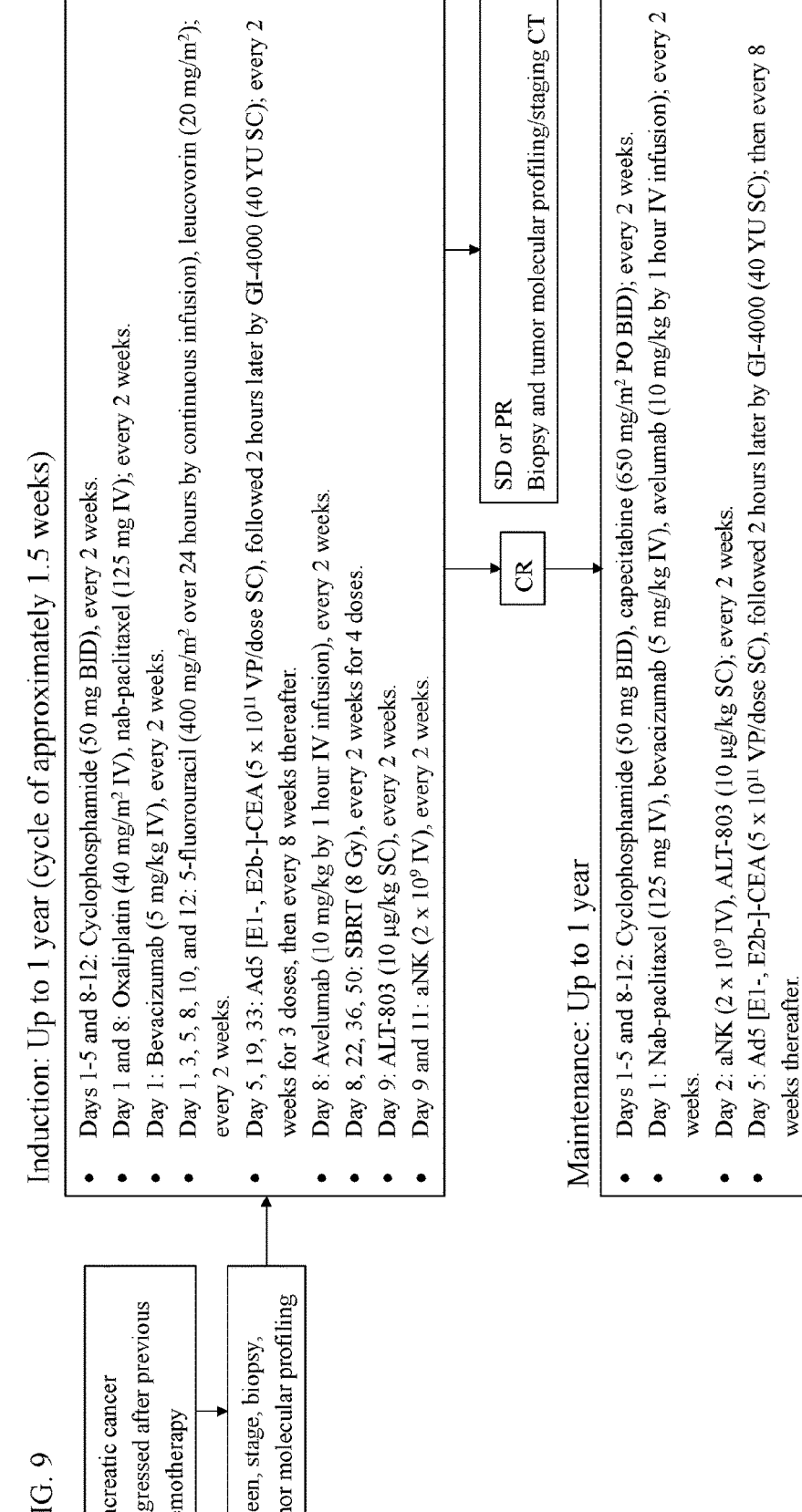

Pancreatic cancer progressed after previous chemotherapy

Screen, stage, biopsy, tumor molecular profiling

Induction: Up to 1 year (cycle of approximately 1.5 weeks)

- Days 1-5 and 8-12: Cyclophosphamide (50 mg BID), every 2 weeks.
- Day 1 and 8: Oxaliplatin (40 mg/m² IV), nab-paclitaxel (125 mg IV); every 2 weeks.
- Day 1: Bevacizumab (5 mg/kg IV), every 2 weeks.
- Day 1, 3, 5, 8, 10, and 12: 5-fluorouracil (400 mg/m² over 24 hours by continuous infusion), leucovorin (20 mg/m²); every 2 weeks.
- Day 5, 19, 33: Ad5 [E1-, E2b-]-CEA (5 x 10¹¹ VP/dose SC), followed 2 hours later by GI-4000 (40 YU SC); every 2 weeks for 3 doses, then every 8 weeks thereafter.
- Day 8: Avelumab (10 mg/kg by 1 hour IV infusion), every 2 weeks.
- Day 8, 22, 36, 50: SBRT (8 Gy), every 2 weeks for 4 doses.
- Day 9: ALT-803 (10 µg/kg SC), every 2 weeks.
- Day 9 and 11: aNK (2 x 10⁹ IV), every 2 weeks.

CR

SD or PR
Biopsy and tumor molecular profiling/staging CT

Maintenance: Up to 1 year

- Days 1-5 and 8-12: Cyclophosphamide (50 mg BID), capecitabine (650 mg/m² PO BID); every 2 weeks.
- Day 1: Nab-paclitaxel (125 mg IV), bevacizumab (5 mg/kg IV), avelumab (10 mg/kg by 1 hour IV infusion); every 2 weeks.
- Day 2: aNK (2 x 10⁹ IV), ALT-803 (10 µg/kg SC); every 2 weeks.
- Day 5: Ad5 [E1-, E2b-]-CEA (5 x 10¹¹ VP/dose SC), followed 2 hours later by GI-4000 (40 YU SC); then every 8 weeks thereafter.

METHODS OF TREATING CANCER

CROSS REFERENCE TO RELATED APPLICATIONS

This application is a national stage application under 35 U.S.C. 371 and claims the benefit of PCT Application No. PCT/US2020/062334 having an international filing date of 25 Nov. 2020, which designated the United States, and which PCT application claims the benefit of priority under 35 U.S.C. § 119 (e) to U.S. Provisional Patent Application Ser. No. 62/941,376, filed 27 Nov. 2019, the entire disclosures of each of which are incorporated herein by reference.

REFERENCE TO SEQUENCE LISTING

This application contains a Sequence Listing submitted as an electronic txt file named "8774-10-PUS_Seq_Listing_ST25.txt", having a size in bytes of 10,132 bytes, and created on Aug. 29, 2025. The information contained in this electronic XML file is hereby incorporated by reference in its entirety.

FIELD OF THE INVENTION

This treatments described herein relate generally to the role of T cell receptor diversity in multimodal cancer immunotherapy.

BACKGROUND OF THE INVENTION

This section includes information that may be useful in understanding the methods described and claimed herein. This section is not an admission that any of the information provided herein is prior art, or that any publication specifically or implicitly referenced is prior art.

Cancer is frequently unresponsive to therapy. Methods of cancer treatment should, therefore, include a determination of how most effectively to administer therapy. Effective therapy administration can involve continuing the same treatment, altering the treatment, and/or discontinuing treatment. Effective therapy administration can also involve discontinuing one treatment in favor of another.

Cancer immunotherapies use the patient's immune system to fight against the patient's cancer. Cancer therapies can be administered in combinations, for example as a multimodal cancer immunotherapy. Some cancer therapies, including immunotherapies, can act synergistically in combinations. It is important to know which treatments to use, when to use the treatments, and how to administer the treatment. Cancer treatment methods can thus comprise methods to help those administering treatment know how to proceed once treatment has started. For example, methods to determine whether a cancer treatment is working and/or will work improve treatment.

BRIEF DESCRIPTION OF THE DRAWINGS

FIG. 2 shows progression-free survival (PFS) in study patients over time.

FIG. 9 illustrates a study treatment schema for pancreatic cancer.

SUMMARY

Figure 1:
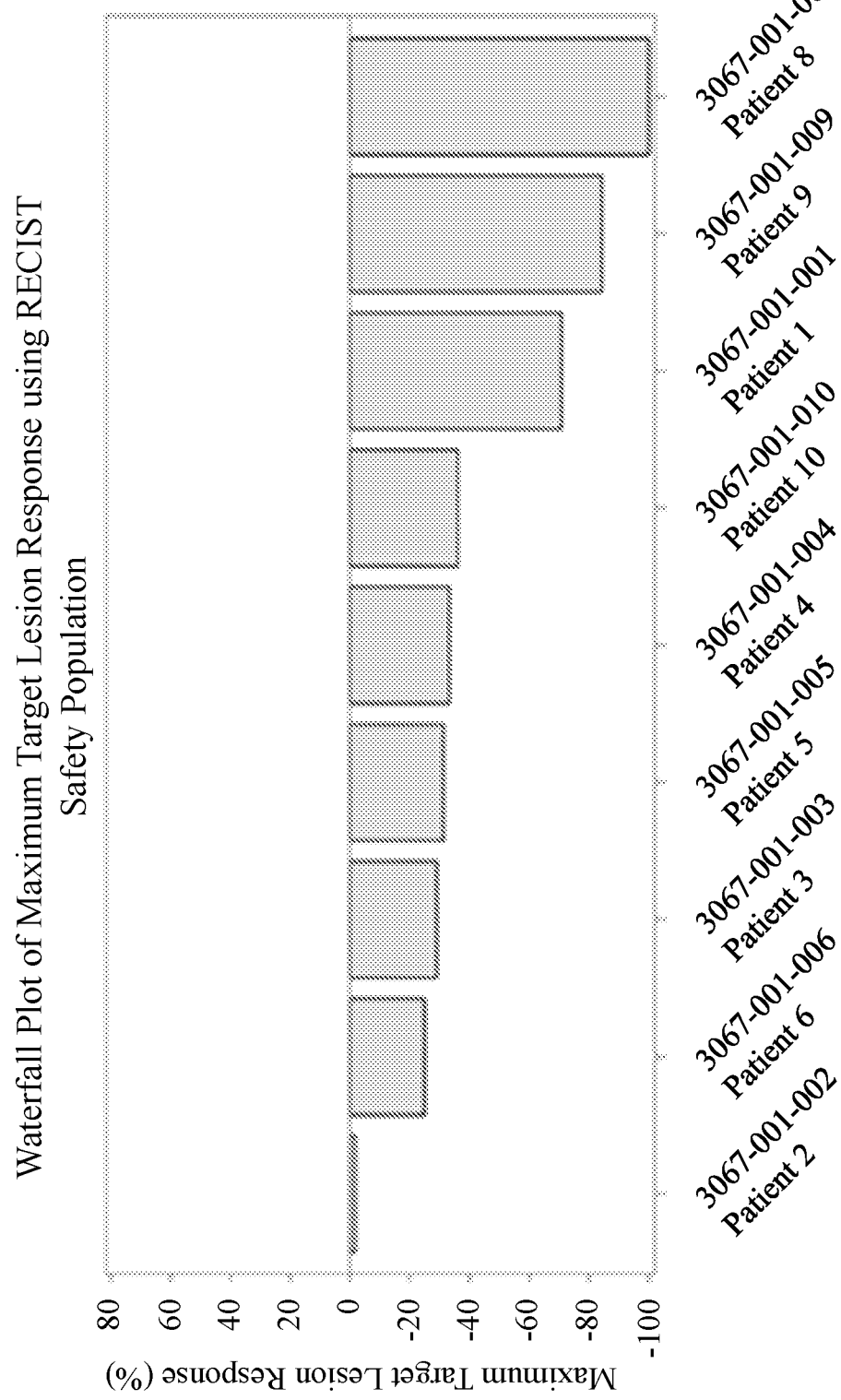
FIG. 1 shows a waterfall plot of maximum target lesion response.

The methods described herein are useful for determining likely effectiveness of cancer treatments. Cancer treatments—particularly immunotherapies—benefit from a patient's healthy immune system. TCR diversity is important for the immune system. High TCR diversity is associated with positive immunological outcomes, and low diversity with adverse outcomes.

In some embodiments, the methods described herein treat cancer in a patient who has been receiving multimodal cancer immunotherapy for at least two months. These methods include administering multimodal immunotherapy when the TCR diversity in patient blood increases at least 3-fold between a first time point and a second time point at least two months after the first time point. In one embodiment, TCR diversity in patient blood is determined before initiation of the multimodal cancer immunotherapy. In another embodiment, TCR diversity is determined two months after initiation of the multimodal cancer immunotherapy. In another embodiment, TCR diversity is determined at any arbitrary point in the course of immunotherapy, with measurements taken at least two months apart from each other.

In some embodiments, TCR diversity increases at least 4 fold, 5 fold, 6 fold, 7 fold, 8 fold, 9 fold, 10 fold, 11 fold, 12 fold, 13 fold, 14 fold, or 15 fold between the first and second time points. In some embodiments, the multimodal cancer immunotherapy treatment is continued if the TCR diversity increases at least 4-fold, 5-fold, 6-fold, 7-fold, 8-fold, 9-fold, 10-fold, 11-fold, 12-fold, 13-fold, 14-fold, or 15-fold between the first and second time points.

In some embodiments, the multimodal cancer immunotherapy treatment is discontinued if the TCR diversity does not increase at least 15-fold, 14-fold, 13-fold, 12-fold, 11-fold, 10-fold, 9-fold, 8-fold, 7-fold, 6-fold, 5-fold, 4-fold, 3-fold, 2-fold, or 1.5-fold between the first and second time points. Discontinuation of multimodal immunotherapy can include stopping all immunotherapy, adding one or more immunotherapies, stopping one or more immunotherapies, or adjusting the administration of one or more immunotherapies, even if a cancer therapy other than the immunotherapy is continued or initiated.

In some embodiments, TCR diversity is assessed by polymerase chain reaction (PCR). The PCR is reverse-transcriptase PCR in certain embodiments.

In some embodiments, the multimodal cancer immunotherapy comprises two or more immunotherapies selected from the group consisting of therapies that mitigate immunosuppression on the tumor microenvironment, therapies that induce immunogenic cell death signals, therapies that coordinate immunogenic cell death signals, therapies that condition dendritic cells, therapies that condition T cells, therapies that enhance innate immune responses, and therapies that maintain immune responses. In some embodiments, the cancer immunotherapy comprises two or more immunotherapeutics selected from the group consisting of aldoxorubicin, N-803, ETBX-011, ETBX-051, ETBX-061, GI-4000, GI-6207, GI-6301, NK cells, avelumab, bevaci-zumab, capecitabine, cisplatin, cyclophosphamide, 5-fluo-rouracil, leucovorin, nab-paclitaxel, and stereotactic body radiation therapy (SBRT). In some embodiments, the cancer immunotherapy comprises an NK cell selected from the group consisting of aNK, haNK, taNK, and t-haNK (see, copending application PCT/US2019/044637).

In some embodiments, the cancer immunotherapy com-prises two or more immunotherapies selected from the group consisting of a viral vector expressing an antigen, a yeast immunotherapy, a low dose chemotherapy, a low dose radiation therapy, an immune checkpoint inhibitor, and an IL-15 superagonist. The low dose chemotherapy can be low dose metronomic chemotherapy. Low dose chemotherapy is considered to be immunotherapy, while standard chemo-therapy (also known as traditional chemotherapy or cyto-toxic chemotherapy) is not immunotherapy. Low dose radia-tion therapy is considered to be immunotherapy, while standard (i.e. high dose) radiation therapy is not immuno-therapy. In some embodiments, the patient is administered at least one cancer therapy that is not an immunotherapy.

In some embodiments, the cancer is selected from the group consisting of lung cancer, skin cancer, brain cancer, spinal cord cancer, breast cancer, colon cancer, rectal cancer, liver cancer, pancreatic cancer, head & neck cancer, gall bladder cancer, ovarian cancer, urothelial cancer, and blood cancer. In some embodiments, the cancer is selected from the group consisting of non-small-cell lung carcinoma (NSCLC), triple negative breast cancer (TNBC), head and neck squamous cell carcinoma (HNSCC), pancreatic adeno-carcinoma, chordoma, melanoma, Merkel cell carcinoma, non-Hodgkin lymphoma, acute myelogenous leukemia, myelodysplastic syndrome, neuroblastoma, and glioblas-toma.

In some embodiments, TCR diversity is calculated as a Shannon Wiener diversity index. In some embodiments, TCR diversity is calculated for CDR3 regions from TCR $\alpha/\beta$ chains. In some embodiments, TCR diversity is calculated for RNA sequences encoding CDR3 regions from TCR $\alpha/\beta$ chains.

DETAILED DESCRIPTION

Cancer and the immune system. The immune system plays a dual role in cancer, both protecting against cancer development and promoting cancer progression by selecting for tumor cells that can escape immune destruction. This paradoxical role of the immune system in cancer is known as "cancer immunoediting." See, Schreiber & al. (2011) Science 331:1565-70. Immunoediting includes 3 phases: (1) elimination, in which immune cells detect and eliminate tumor cells; (2) equilibrium, in which cancer killing bal-ances tumor growth; and (3) escape, in which tumor cells evade immune defenses and grow rapidly.

Cancer cells modulate tumor microenvironment (TME) through recruitment of regulatory T cells (Tregs), myeloid-derived suppressor cells (MDSCs), and immunosuppressive macrophages (M2 macrophages). Cancer cells also evade immune surveillance by down-regulating certain major his-tocompatibility complex (MHC) molecules, which are typi-cally essential for T cells to recognize tumor-associated antigens (TAAs).

Traditional, molecularly uninformed treatment regimens of maximum tolerated dose (MTD) based chemotherapy, targeted therapy based on cancer marker signatures, and even monoclonal antibody therapy with high dose radiation impair the immune system, thereby generating tolerogenic cell death. Unfortunately, tolerogenic tumor cell death enables evasion of cancer immunosurveillance and facili-tates selection and escape of multiple resistant, heterogenic clones, with resultant metastasis and poor long term out-comes in multiple tumor types.

The Nant Cancer Vaccine as described in Example 1 below (see also, WO 18/5973) is a multimodal cancer immunotherapy designed to address, amongst other things, aspects of cancer that allow immune evasion. The Nant Cancer Vaccine combines treatments that coordinate immune response to prevent immune evasion. The Nant Cancer Vaccine, and other multimodal cancer therapies, use various aspects of the immune system to attack cancer.

"Multimodal cancer immunotherapy" refers to cancer therapy comprising two or more immunotherapies selected from the group consisting of therapies that mitigate immu-nosuppression on the tumor microenvironment, therapies that induce immunogenic cell death signals, therapies that coordinate immunogenic cell death signals, therapies that condition dendritic cells, therapies that condition T cells, therapies that enhance innate immune responses, and thera-pies that maintain immune responses. Immunotherapies use the patient's own immune system, while standard cancer therapies generally act through other mechanisms. For example, chemotherapies, surgery, and radiation typically treat cancer through mechanisms that do not involve stimu-lating the patient's immune system to attack cancer.

Various immunotherapy combinations qualify as multi-modal cancer immunotherapies. Multimodal cancer immu-notherapies include two or more cancer immunotherapies, and, optionally, one or more other types of cancer therapy simultaneously. As described herein, multimodal cancer immunotherapy is discontinued during treatment if certain criteria relating to T cell receptor diversity are not met. Discontinuation can include, for example, adding or remov-ing one or more component therapies from the multimodal cancer immunotherapy and/or adjusting dosages or timing of administration of one or more component therapies of the multimodal cancer immunotherapy. Other alterations to multimodal cancer immunotherapies are also possible.

T cell receptor diversity. Various molecular mechanisms generate initial TCR diversity, including genetic recombi-nation at multiple sites. Naïve T cells circulate and encounter antigen. Upon exposure to antigen, cells expressing immu-nological receptors having desired binding properties are expanded, and undergo further sequence modification (e.g., somatic hypermutation & additional recombination). There can also be negative selection, where cells expressing immu-nological receptors having undesirable binding properties (e.g., self-reactivity) are removed.

The TCR repertoire is highly plastic and can create TCRs with broad diversity and selectivity. A TCR is a heterodimer, each chain of which is a member of the immunoglobulin superfamily. Each chain has an N-terminal variable (V) domain, and a C-terminal constant (C) domain. The TCR V$\alpha$-chain and V$\beta$-chain each have three hypervariable or complementarity determining regions (CDRs). The V$\beta$-chain has an additional area of hypervariability (HV4) that does not normally contact antigen. The intersection of specific regions (V/J for $\alpha$ or $\gamma$ chains, V/D/J for $\beta$ or $\delta$ chains) corresponds to the CDR3 region that is important for antigen-MHC recognition. It is the unique combination of the segments at this region, along with palindromic and random N- and P-nucleotide additions, which accounts for the TCR repertoire.

TCR diversity indices can interrogate the distribution of clonotypes within the TCR repertoire, providing information on the number of different clonotypes, the absolute quantity of each clonotype, and/or the relative frequency distribution of clonotypes. There are many different diversity indices: the Shannon-Wiener diversity index (also known as Shannon entropy or Shannon-Weaver index), Renyi entropy, Simpson index, Berger-Parker index, and others.

The Shannon Wiener Diversity Index is represented by the following equation:

$$H' = -\sum_{i=I}^{s} \frac{n_i}{N} \ln \frac{n_i}{N}$$

where N is the number of unique clonotypes and n is the number of times the ith clonotype was detected.

Surprisingly, it is revealed herein that the change in TCR diversity over time predicts a patient's response to cancer therapy, in particular multimodal cancer immunotherapy. To date, it has been difficult to determine how to use immunotherapy most effectively, including which treatments to use and when. As revealed herein, TCR receptor diversity analysis is a valuable addition to a patient's cancer therapy. For example, TCR diversity analysis can inform whether to continue, modify, or halt treatment.

In some embodiments, TCR diversity is assessed by polymerase chain reaction (PCR). The PCR method can be reverse-transcriptase PCR. Methods for PCR, including reverse transcriptase PCR (also known as RT-PCR), are well known in the art. See, e.g., Garibyan & Avashia (2013) *J. Invest. Dermatol.* 133(3):1-4. Exemplary PCR methods include digital PCR, RT PCR, quantitative PCR, real-time PCR, isothermal amplification, linear amplification, or isothermal linear amplification, quantitative fluorescent PCR (QF-PCR), multiplex fluorescent PCR (MF-PCR), single cell PCR, restriction fragment length polymorphism PCR (PCR-RFLP), PCR-RFLP/RT-PCR-RFLP, hot start PCR, nested PCR, in situ colony PCR, in situ rolling circle amplification (RCA), bridge PCR (bPCR), picotiter PCR, droplet digital PCR, or emulsion PCR (emPCR). Other suitable amplification methods include ligase chain reaction (LCR (oligonucleotide ligase amplification (OLA)), transcription amplification, cycling probe technology (CPT), molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), transcription mediated amplification (TMA), degenerate oligonucleotide-primed PCR (DOP-PCR), multiple-displacement amplification (MDA), strand displacement amplification (SDA), and nucleic acid based sequence amplification (NABSA). Other amplification methods that can be used herein include those described in U.S. Pat. Nos. 5,242,794; 5,494,810; 4,988, 617; & 6,582,938.

TCR diversity is assessed at two or more time points in some embodiments. In those embodiments, TCR diversity can be compared at multiple time points. For example, TCR diversity can be assessed at a first time point and a second time point, and the TCR diversity at the two time points can be compared. Comparison of TCR diversity at multiple time points can be used to evaluate multimodal immunotherapeutic efficacy. The multimodal cancer immunotherapy can then be continued or discontinued—where discontinuing includes changing or stopping the multimodal cancer immunotherapy—based on that evaluation. In some embodiments, the multimodal cancer immunotherapy treatment is continued if the TCR diversity increases at least 4-fold, 5-fold, 6-fold, 7-fold, 8-fold, 9-fold, 10-fold, 11-fold, 12-fold, 13-fold, 14-fold, or 15-fold between the first and second time points. In some embodiments, the multimodal cancer immunotherapy treatment is discontinued if the TCR diversity does not increase at least 15-fold, 14-fold, 13-fold, 12-fold, 11-fold, 10-fold, 9-fold, 8-fold, 7-fold, 6-fold, 5-fold, 4-fold, 3-fold, 2-fold, or 1.5-fold between the first and second time points.

In certain embodiments, TCR diversity of a patient can be assessed at more than one time point. For example, T cell receptor diversity can be assessed at times of about 1 week, 2 weeks, 3 weeks, 4 weeks, 1 month, 2 months, 3 months, 4 months, 5 months, 6 months, 7 months, 8 months, 9 months, 10 months, 11 months, 12 months, 13 months, 15 months, 18 months, 2 years, 3 years, 4 years or more apart. T cell receptor diversity can also be assessed at times of at least about 1 week, 2 weeks, 3 weeks, 4 weeks, 1 month, 2 months, 3 months, 4 months, 5 months, 6 months, 7 months, 8 months, 9 months, 10 months, 11 months, 12 months, 13 months, 15 months, 18 months, 2 years, 3 years, 4 years or more apart. T cell receptor diversity can also be assessed at times of at most about 1 week, 2 weeks, 3 weeks, 4 weeks, 1 month, 2 months, 3 months, 4 months, 5 months, 6 months, 7 months, 8 months, 9 months, 10 months, 11 months, 12 months, 13 months, 15 months, 18 months, 2 years, 3 years, 4 years or more apart.

In certain embodiments, TCR diversity can be assessed at various time points before or during treatment. In certain embodiments, TCR diversity can be assessed before the initiation of the multimodal cancer immunotherapy. In other embodiments, TCR diversity can also be assessed at the initiation—or shortly after initiation—of multimodal cancer immunotherapy. For example, TCR diversity can be assessed on multimodal cancer immunotherapy initiation day. In certain embodiments, TCR diversity can also be assessed at later time points after initiation of a multimodal cancer immunotherapy.

In certain embodiments, TCR diversity can be assessed after initiation of a multimodal cancer immunotherapy, for example to evaluate the effectiveness of the multimodal cancer immunotherapy. For example, TCR diversity can be assessed before initiation of a multimodal cancer immunotherapy and then again at a second time point after initiation of the multimodal cancer immunotherapy. One can then compare the multiple TCR diversity assessments to evaluate multimodal cancer immunotherapy efficacy. The multimodal immunotherapy efficacy evaluation can then be used to decide whether to continue or discontinue multimodal immunotherapy.

In some embodiments, a patient's TCR diversity is assessed after the patient receives multimodal cancer immunotherapy. TCR diversity can be assessed at times of about 1 week, 2 weeks, 3 weeks, 4 weeks, 1 month, 2 months, 3 months, 4 months, 5 months, 6 months, 7 months, 8 months, 9 months, 10 months, 11 months, 12 months, 13 months, 15 months, 18 months, 2 years, 3 years, 4 years, or more after immunotherapy initiation. In certain embodiments, TCR diversity can also be assessed at least about 1 week, 2 weeks, 3 weeks, 4 weeks, 1 month, 2 months, 3 months, 4 months, 5 months, 6 months, 7 months, 8 months, 9 months, 10 months, 11 months, 12 months, 13 months, 15 months, 18 months, 2 years, 3 years, 4 years, or more after immunotherapy initiation. In certain embodiments, TCR diversity can also be assessed at most about 1 week, 2 weeks, 3 weeks, 4 weeks, 1 month, 2 months, 3 months, 4 months, 5 months, 6 months, 7 months, 8 months, 9 months, 10 months, 11 months, 12 months, 13 months, 15 months, 18 months, 2 years, 3 years, 4 years or more after immunotherapy initiation.

In one embodiment, as sample treatment regimen is as follows. A TNBC that has progressed on or after Standard of Care (SoC) therapy can be screened and staged by biopsy and tumor molecular profiling.

Induction (Up to 1 Year, Cycle of Approximately 2 Weeks)

Day 1: Bevacizumab (5 mg/kg IV; for the first 2 cycles only), leucovorin (20 mg/m$^2$ IV bolus), nab-paclitaxel (125 mg IV), and cisplatin (32 mg/m$^2$ IV); every 3 weeks.

Days 1-5: 5-FU (1500 mg/m$^2$ continuous IV infusion over 85-96 hours) and cyclophosphamide (25 mg PO BID); every 3 weeks.

Day 5 (+1 day): Ad5-based vaccines ($1 \times 10^{11}$ VP/vaccine/dose SC), yeast-based vaccines (40 YU/vaccine/dose SC); every 3 weeks for 3 cycles then every 9 weeks thereafter. Ad5-based vaccines include ETBX-011, ETBX-051, and ETBX-061. Yeast-based vaccines include GI-4000, GI-6207, and GI-6301. Prospective tumor molecular profiling determines if GI-4000 is administered.

Day 8: Aldoxorubicin HCl (100 mg/m$^2$ IV); every 3 weeks.

Day 8-12: Cyclophosphamide (25 mg PO daily); every 3 weeks.

Days 8 and 15: SBRT (maximum of 8 Gy), every 3 weeks for up to 4 cycles.

Day 9: Avelumab (10 mg/kg IV), N-803 (15 µg/kg SC); every 3 weeks

Days 9, 11, and 16: haNK ($2 \times 10^9$ cells/dose IV); every 3 weeks.

Day 15: Nab-paclitaxel (100 mg IV); every 3 weeks. Nab-paclitaxel is given concurrently with SBRT on day 15 and can be given on day 16 once SBRT is completed.

Subjects with SD or PR at regular imaging assessments (every 8 weeks) continue treatment in induction for up to 1 year. Subjects with SD or PR after 1 year may enter maintenance phase.

Maintenance (Up to 1 Year)

Day 1: Aldoxorubicin HCl (60 mg/m$^2$ IV) and nab-paclitaxel (100 mg IV).

Days 1-5: Cyclophosphamide (25 mg PO BID).

Days 1, 3, and 5: Capecitabine (650 mg/m$^2$ PO BID, up to a maximum of 1,000 mg per dose).

Day 2: N-803 (15 µg/kg SC), haNK ($2 \times 10^9$ cells/dose IV), and avelumab (10 mg/kg IV).

Day 5: Ad5-based vaccines ($1 \times 10^{11}$ VP/vaccine/dose SC); yeast-based vaccines (40 YU/vaccine/dose SC); and every 8 weeks thereafter.

Days 8-12: Cyclophosphamide (25 mg PO daily).

Days 15-28: Rest period

EXAMPLES

Example 1. Nant Cancer Vaccine. The following description provides exemplary protocols to treat cancer in a patient with a multimodal cancer immunotherapy. It should be understood that while these protocols list specific compounds and compositions alone or in combination, various alternative compounds and compositions may be provided with the same or similar effect. Moreover, dosage and schedules may change according to patient age, stage of cancer, and overall health condition. Table 1 includes the treatments used in one embodiment of the Nant Cancer Vaccine.

TABLE 1

| Treatments used in a multimodal cancer vaccine study | |
| --- | --- |
| Arm | Intervention/treatment |
| Experimental: Nant TNBC Vaccine | Drug: aldoxorubicin HCl |
| | Biological: N-803 (recombinant human IL-15 super agonist) |
| | Biological: ETBX-011: Ad5 [E1-, E2b-]-CEA vaccine |
| | Biological: ETBX-051: Ad5 [E1-, E2b-]-Brachyury vaccine |
| | Biological ETBX-061: Ad5 [E1-, E2b-]-MUC1 vaccine |
| | Biological: GI-4000 (recombinant *S. cerevisiae* expressing mutant Ras) |
| | Biological: GI-6207 (recombinant *S. cerevisiae* expressing mutant CEA) |
| | Biological: GI-6301 (recombinant *S. cerevisiae* expressing mutant Brachyury) |
| | Biological: haNK (NK-92 [CD16.158V, ER IL-2]) |
| | Biological: avelumab (human anti-PD-L1 IgG1 mAb) |
| | Biological: bevacizumab (human anti-VEGF IgG1 mAb) |
| | Drug: capecitabine |
| | Drug: cisplatin |
| | Drug: cyclophosphamide |
| | Drug: 5-fluorouracil (5-FU) |
| | Drug: leucovorin |
| | Drug: nab-paclitaxel |
| | Procedure: Stereotactic Body Radiation Therapy |

Pharmaceutical agents and compositions: Unless otherwise noted herein, all of the compounds and compositions referred herein are known and commercially available. The compounds that are not commercially available are characterized as listed below.

N-803 (also known as ALT-803 or nogapendekin-alfa-inbakicept) is an IL-15-based immunostimulatory protein complex comprising two protein subunits of a human IL-15 variant associated with high affinity to a dimeric human IL-15 receptor α (IL-15Rα) sushi domain/human IgG1 Fc fusion protein. The IL-15 variant the mature human IL-15 cytokine sequence (114 amino acids), with an asparagine to aspartate substitution at position 72 (N72D). The human IL-15Rα sushi domain/human Fc fusion protein comprises the sushi domain of the human IL-15 receptor a subunit (IL-15Rα) (amino acids 1-65 of the mature human IL-15Rα protein) linked to the human IgG1 CH2-CH3 region containing the Fc domain (232 amino acids). Except for the N72D substitution, all of the protein sequences are human. N-803 is an IL-15 superagonist.

aNK: The aNK cell line is a human, IL-2-dependent NK cell line that was established from the peripheral blood mononuclear cells (PBMCs) of a 50-year-old male diagnosed with non-Hodgkin lymphoma. Gong & al. (1994) *Leukemia* 8:652-58. aNK cells express CD56bright and CD2, but not CD3, CD8, and CD16. A CD56bright/CD16$^{-/low}$ phenotype is typical for a minor subset of NK cells in peripheral blood, which have immunomodulatory functions as cytokine producers. Unlike normal NK cells, aNK does not express most killer cell immunoglobulin-like receptors (KIRs). Only KIR2DL4, a KIR receptor with activating function and inhibitory potential that is expressed by all NK cells, is detected on aNK surfaces. KIR2DL4 mediates inhibition through binding to the HLA allele G.

haNK: The haNK cells are NK-92 [CD16.158V, ER IL-2] derivatives (high-affinity activated natural killer cell line, [haNK™ for Infusion]) and cultured as a human, allogeneic, NK cell line. haNKs produce endogenous, intracellularly retained IL-2 and express CD16, the high-affinity (158V) Fc gamma receptor (FcγRIIIa/CD16a). Phenotypically, the haNK cell line is CD56$^+$/CD3$^-$/CD16$^+$.

taNK: taNK cells are a variety of NK cells that each incorporate a given chimeric antigen receptors (CARs). CAR expression enables taNKs to target tumor-specific antigens on cancer cell surfaces.

t-haNK: t-haNK cells combine haNK and taNK platforms in a single cell. t-haNK cells incorporate a high binding affinity receptor that binds to an administered antibody, designed to enhance the cancer cell killing effect of that antibody, and a CAR to target tumor-specific antigens found on cancer cell surfaces.

Avelumab: Avelumab is a human monoclonal IgG1 that blocks interaction between PD-L1 and its receptor, PD-1, while leaving intact interactions between PD-L2 and PD-1.

ETBX-011 (Ad5 [E1-, E2b-]-CEA(6D)): ETBX-011 is an Ad5-based adenovirus vector vaccine in which the E1, E2b and E3 gene regions have been removed and replaced with a gene encoding CEA with the CAP1-6D mutation.

ETBX-021: ETBX-021 is a HER2-targeting adenovirus vector vaccine comprising the Ad5 [E1-, E2b-] vector and a modified HER2 gene insert. The HER2 gene insert encodes a truncated human HER2 protein that comprises the extracellular domain and transmembrane regions. The entire intracellular domain, containing the kinase domain that leads to oncogenic activity, is removed.

ETBX-051 (Ad5 [E1-, E2b-]-Brachyury): ETBX-051 is an Ad5-based adenovirus vector vaccine that has been modified by the removal of the E1, E2b, and E3 gene regions and the insertion of a modified human Brachyury gene. The modified Brachyury gene contains agonist epitopes designed to increase cytotoxic T lymphocyte (CTL) antitumor immune responses.

ETBX-061 (Ad5 [E1-, E2b-]-MUC1): ETBX-061 is an Ad5-based adenovirus vector vaccine that has been modified by the removal of the E1, E2b, and E3 gene regions and the insertion of a modified human MUC1 gene. The modified MUC1 gene contains agonist epitopes designed to increase CTL antitumor immune responses. See e.g., Oncotarget. 2015; 6:31344-59.

GI-4000: GI-4000 is 4 separate products from the GI-4000 series, GI-4014, GI-4015, GI-4016, GI-4020. Each of these is a recombinant, heat-inactivated *S. cerevisiae* engineered to express a combination of 2 or 3 of 6 mutated Ras oncoproteins. GI-4014, GI-4015, and GI-4016 products each contain two mutations at codon 61 (Q61R & Q61L), plus one of three different mutations at codon 12 (G12V, G12C, or G12D). GI-4020 contains two mutations at codon 61 (Q61H & Q61L), plus one mutation at codon 12 (G12R). GI-4000 is formulated in phosphate buffered saline (PBS) for injection and vialed separately at a concentration of 20 YU/mL (1 YU=$10^7$ yeast cells). Each single use 2 mL vial contains 1.2 mL of biologic product. Two vials of drug product will be used for each GI-4000 administration visit. Two syringes of 0.5 mL will be drawn from each vial, and 4 total injections will be administered for a dose of 40 YU at each dosing visit.

GI-6207: GI-6207 is a heat-killed, recombinant *S. cerevisiae* vaccine engineered to express the full length human carcinoembryonic antigen (CEA), with a modified gene coding sequence to code for a single amino acid substitution (N610D), which is designed to enhance immunogenicity.

GI-6301: GI-6301 is a heat-killed, *S. cerevisiae* vaccine expressing the human Brachyury (hBrachyury) oncoprotein. The Brachyury antigen is the full-length protein possessing an N-terminal MADEAP (Met-Ala-Asp-Glu-Ala-Pro) motif appended to the hBrachyury sequence to promote antigen accumulation within the vector and a C-terminal hexahistidine epitope tag for analysis by Western blotting. Expression of hBrachyury is controlled by a copper-inducible CUP1 promoter.

"Yeast immunotherapy" refers to yeast that express and/or contain heterologous proteins or nucleic acid sequences from cancer associated antigens or other antigens that can be used to stimulate an immune response. Yeast immunotherapies include but are not limited to GI-4000, GI-4014, GI-4015, GI-4016, GI-4020, GI-6207, & GI-6301.

Head and Neck Squamous Cell Cancer (HNSCC): HNSCCs encompass numerous malignant tumors in the throat, larynx, nose, sinuses, and mouth. Approximately 60,000 patients are diagnosed with HNSCC annually in the U.S. Roughly half of all HNSCC patients die of the disease. Despite various treatments, there remains an urgent need to improve treatment outcome and overall survival.

In general, the HNSCC vaccine treatment presented herein seeks to maximize immunogenic cell death (ICD) and augment and maintain the innate and adaptive immune responses against cancer cells. The rationale for the selection of agents is summarized in Table 2.

11

TABLE 2

Rationale for Selection of Agents in Nant TNBC Protocol

| Agent | Mitigating Immuno-suppression in the TME | Inducing and Co-ordina-ting ICD Signals | Con-ditioning Dendritic and T Cells | Enhan-cing Innate Immune Response | Maintain-ing Immune Responses |
|---|---|---|---|---|---|
| Aldoxorubicin HCl | X | X | | | |
| Avelumab | | | | | |
| Bevacizumab | X | X | | | |
| Capecitabine | X | X | | | |
| Cisplatin | | X | | | |
| Cyclophos-phamide | X | X | | | |
| ETBX-011 | | | X | | |
| ETBX-051 | | | X | | |
| ETBX-061 | | | X | | |
| 5-FU/leucovofin | X | X | | | |
| GI-4000 | | | X | | |
| GI-6207 | | | X | | |
| GI-6301 | | | X | | |
| haNK cells | | | | X | |
| N-803 | | | X | X | X |
| Nab-paclitaxel | X | X | | | |
| SBRT | | X | | X | |

Table 2 lists the mechanism(s) by which each agent impacts the immune system, consequently leading to ICD. Combining agents that simultaneously (or sequentially) target distinct but complementary mechanisms that enable tumor growth maximizes maximize anticancer activity and prolongs treatment response duration.

To that end, contemplated HNSCC treatments combine low dose metronomic chemotherapy (LDMC), bevacizumab, cetuximab, cancer vaccine(s), low-dose radiation therapy, an IL-15 superagonist, NK cell therapy, and a checkpoint inhibitor. Such treatment regimen maximizes ICD and augments/maintains the innate and adaptive immune responses against cancer cells. More specifically, the treatment regimen interrupts the immunoediting escape phase by (a) mitigating immunosuppression in the TME; (b) inducing and coordinating ICD signals; (c) conditioning dendritic and T cells; (d) enhancing innate immune responses; and (e) maintaining immune responses. A checkpoint inhibitor will be used to promote long-term anticancer immune responses.

Example 2. NANT TNBC Vaccine. TNBC is an aggressive breast cancer subtype with limited treatment options. Immunotherapy has demonstrated clinical benefit in selected TNBC patients. Schmid & al. (2018) *N. Engl. J. Med.* 379(22):2108-21. Rationally-based, sequenced orchestration of both innate and adaptive immune system responses can elicit anti-tumor efficacy. By activating the entire immune system, immunogenic cell death in TNBC will be durable and will incur few adverse events. This is a first-in-human combination immunotherapy protocol of chemo-radiation, checkpoint inhibition, cytokine-induced NK & T cell activation, and off-the-shelf high-affinity NK (haNK) cell infusion. Margolin & al. (2018) *Clin. Cancer. Res.* 24:5552-61.

Methods. TNBC patients for enrollment in QUILT-3.067 (NCT03387085) had: (1) either progressed on or after (or refused) anthracycline-based chemotherapy (or other standard of care (SoC)) or other taxane- and platinum-based therapies; (2) an ECOG performance status of 0 to 2; & (3) had at least 1 lesion of ≥1.0 cm. Subject tumor tissue was biopsied for molecular analysis and blood samples collected for isolation of peripheral blood mononuclear cells (PBMCs). Table 2 shows the rationale for agent selection.

Demographics, Adverse Events (AEs) & toxicity. Table 3 shows characteristics of the nine TNBC patients treated. Eight of these had primarily chemotherapy-related neutropenia and/or anemia. Grade≥3 haNK-related AEs (fever and fatigue) were observed in 3 patients. No severe adverse events (SAEs) were attributed to investigational agents. No patients experienced cytokine release syndrome.

TABLE 3

Demographics, AEs, & Toxicity

| Demographics | N (%) | Grade 3 AEs | N (%) |
|---|---|---|---|
| Age | 49 (36-57) | Subjects with at least 1 | 9 (100) |
| Caucasian | 6 (67) | grade 3 or higher AE | |
| Hispanic | 2 (22) | Anemia | 5 (56) |
| Asian | 1 (11) | Neutropenia | 6 (67) |
| ECOG: 0, 1 | 7 (78), | Thrombocytopenia | 1 (11) |
| | 2 (22) | Febrile neutropenia | 1 (11) |
| Site of metastasis: | | Nausea | 1 (11) |
| Bone | 4 (44) | Fatigue | 2 (22) |
| Liver | 3 (33) | Pyrexia | 5 (56) |
| Lung | 6 (67) | Cholecystitis | 1 (11) |
| Lymph node | 8 (89) | Infection | 3 (33) |
| Skin | 1 (11) | Hyponatremia | 1 (11) |
| | | Lymphedema | 1 (11) |

Response to treatment & progression-free survival (PFS). FIG. 1 shows the maximum target lesion response percent based on RECIST1.1 criteria for each patient. See, Eisenhauer & al. (2009) *Eur. J. Cancer* 45(2):228-47. The disease control rate (DCR) combining Complete Response (CR), Partial Response (PR), and Stable Disease (SD) is 78% (7 patients of 9). Two patients (22%) achieved a CR. In FIG. 2, PFS based on immune-related response criteria is also shown. The Overall Response Rate (ORR=PR+CR) is 67% (6/9 pts). See, Wolchok & al. (2009) Clin Cancer Res 15(23): 7412-20. Median PFS is 13.7 months. Seven patients remained alive through the study. The duration of responses ranges from 2 months to over 12 months.

TCR diversity in response to treatment. PBMC analysis of CR and PR patients revealed >13× increase in Shannon-Weiner Diversity Index (SWDI) TCR diversity 2 months after treatment initiation relative to pre-treatment baseline (e.g. Patient 1 in Table 7). CR & PR patients also showed increased SWDI thereafter. By contrast, PBMC TCR diversity increased <2× or decreased (e.g. Patient 5 in Table 7) in SD patients. These results demonstrate that ORR to orchestrated treatment in QUILT 3.067 was high, while toxicity was low. Furthermore, TCR diversity is a useful predictive biomarker for response.

Example 3. TCR Repertoire Analysis. PBMCs were isolated from blood collected in tubes by density gradient centrifugation with Ficoll to separate PBMCs from plasma, red blood cells, granulocytes, and other blood components as follows:

Reagents:

Ficoll-Paque PLUS (GE Healthcare Life Sciences Cat #17-1440-02)

Fetal Bovine serum (FBS), heat-inactivated, sterile (Hyclone Cat #SH3007103)

Sterile Hanks Balanced Salt Solution (HBSS), without Calcium and Magnesium (Hyclone Cat #SH30031Fs)

Protocol:

A. Red Top Clot tube:
1. Spin tube at 2000 g at 18-16° C. for 10 minutes.
2. Transfer serum to 15 mL conical.
3. Aliquot 1 mL into a 2 mL Cryovial and freeze at −80° C.

B. PBMC and Plasma Isolation:
1. Pipette 3.3 mL Ficoll to Greiner 12 mL Leucosep tube (VWR Cat #89048-932) with frit.
2. Centrifuge the tubes 1 minute at 800-1000 g at 18-20° C. so the Ficoll settles below the frit.
3. Mix blood in vacutainer tubes by gently inverting tubes in an arc several times.
4. Note the total volume of blood to be processed as it is removed from the vacutainer.
5. Pipette the whole blood directly onto the frit of the Ficoll-loaded Leucosep tubes using a serological pipette. Pipette 3-6 mL of whole blood per tube.
6. Centrifuge for 30 minutes at 800 g with the brake off at 18-26° C.
7. Gentle remove samples from the centrifuge so as not to disturb the layers. Centrifugation results in the tube contents dividing into six distinct layers. From top to the bottom of the tube, these are: 1) plasma, 2) PBMC layer (Lymphocytes and Monocytes), 3) Ficoll, 4) frit, 5) Ficoll, and 6) packed red blood cells and granulocytes
8. Remove most of the plasma using a transfer pipette, leaving approximately 1 cm fluid above the PBMC layer, and place in a 15 ml conical centrifuge tube.
9. Centrifuge the plasma at 800-1000 g for 20 minutes at 18-26° C.
10. Pipette the clarified plasma in 1 mL aliquots into cryovials. Store at −80° C.

C. Wash and Resuspension of PBMC:
1. Transfer PBMC layer to a sterile 15 mL conical centrifuge tube.
2. Dilute the PBMC fraction to approximately 10 mL by adding HBSS and mix to homogeneity.
3. Pellet cells by centrifugation for 10 minutes at 350-400 g at 18-16° C.
4. Discard supernatant without disturbing the cell pellet.
5. Resuspend the cells in approximately 200-500 μL of HBSS.
6. Resuspend the cells in each tube with 5 mL HBSS.
7. Combine all tubes from the same patient/sample into a single 50 ml conical centrifuge tube. Bring the volume to 20 mL with HBSS.
8. Pellet cells by centrifugation for 10 minutes at 350-400 g at 18-16° C.
9. Discard supernatant without disturbing the pellet.
10. Resuspend the cells in approximately 200-500 μL of HBSS.
11. Resuspend in HBSS to 100-125% of the total blood volume. Perform manual count using hemocytometer.

D. Manual Cell Count Using Hemocytometer:
1. Draw 15 μL of the cell suspension and mix with 15 μL dye solution (Trypan Blue and Turk Fluid) in Eppendorf tubes. Do not allow the cells to sit in dye for longer than 5 minutes, as the dye is slowly absorbed by the viable cells leading to falsely elevated non-viable cell count.
2. Load one side of the hemocytometer chamber with cells diluted in Trypan Blue and the other side with cells diluted in Turk Fluid by placing 10 μL of the cell/dye mix at the edge of the "V"-shaped groove of the chamber.

3. View under microscope and count cells. When counting Trypan Blue, do not count red blood cells which are small, brown non-nucleated discoid cells.
4. Using Trypan Blue, count 100 total cells and record the number of viable (unstained) and non-viable (stained) cells on the Hemocytometer Counts Worksheet to determine % Viability.
5. Using Turk Fluid, count total PBMC and record the number of PBMC in each 4×4 corner square of the Hemocytometer to determine the number of cells per mL.

Total RNA was extracted from the PBMCs using Qiagen RNeasy& Micro (Cat. No. 74004) or Mini (Cat. No. 74104) kits according to the manufacturer protocol (Qiagen Supplementary Protocol RY46 Sep-14, incorporated herein by reference). The RNA was then used to generate sequencing libraries as follows.

Starting Materials:

The RNA sample should be free of salts (e.g. $Mg^{2+}$, or guanidine salts) or organics (e.g., phenol and ethanol). High quality RNA with RNA integrity number>7 is recommended. Start with 10 ng-1 μg total RNA (recommended 400-500 ng from whole blood and up to 1 μg from tissue). AMPure XP Beads (Beckman Coulter Item No: A63881) are required throughout the protocol.

Protocol:

A. Reverse Transcription and mRNA Synthesis
1. Mix the following components in a sterile, nuclease-free tube on ice:
Total RNA (10 ng-1 μg) (1-9 μL), AbSeq First Strand Synthesis Reaction Buffer (4×) (5 μL), dNTP mix (2 μL), AbSeq RT primer (1 μL), AbSeq UID oligo pool (1 μL), NEBNext ProtoScript II Enzyme Mix (2 μL), and Nuclease free $H_2O$ (to 20 μL) 2. Add 0.5 μL of Cell Lysis Buffer to each tube. Do not denature RNA.
3. Prepare cDNA products by placing the tube in a thermocycler, with the heated lid set to ≥80° C., and run the following program: 40 minutes at 42° C., 10 minutes at 70° C., and hold at 4° C.

B. Purify the cDNA with Streptavidin Magnetic Beads
1. Dilute 2× Bind and Wash Buffer to 1× with nuclease-free $H_2O$.
2. Aliquot the total amount of Streptavidin Magnetic Beads needed (15 μL of Streptavidin Magnetic Beads per sample) into a clean RNase-free 1.5 mL tube or PCR tube.
3. Place the tube on a magnetic rack at room temperature. Once the solution is clear (~2 minutes) carefully remove and discard supernatant without disturbing the bead pellet.
4. Remove the tube from the magnet and wash the beads by adding 200 μL of 2× Bind and Wash buffer. Vortex briefly to resuspend the beads and quickly spin the tube in a microcentrifuge to collect any sample on the sides of the tube.
5. Place the tube on a magnetic rack. Once the solution is clear, carefully remove and discard the supernatant without disturbing the bead pellet.
6. Repeat Steps 4-5.
7. Remove the tube from the magnetic rack. Resuspend the beads in 20 μL of 2× Bind and Wash buffer for each sample. Vortex briefly to resuspend the beads.
8. Add 20 μL beads to each cDNA product. Vortex briefly to mix.

9. Place the tube on a rotator for 15 minutes at room temperature, or if using PCR tubes, let stand and mix every five minutes.

10. Quickly spin down the tube to collect any sample on the sides of the tube and place the tube on a magnetic rack. Once the solution is clear, carefully remove and discard the supernatant without disturbing the bead pellet.

11. Remove the tube from the magnetic rack. Add 100 μL 1× Bind and Wash buffer (from step 1). Vortex briefly to resuspend the beads.

12. Quickly spin down the tube to collect any sample on the sides and place the tube on a magnetic rack. Once the solution is clear, carefully remove and discard the supernatant without disturbing the bead pellet.

13. Remove the tube from the magnetic rack and add 100 μL 0.1% Tween-20. Vortex briefly to resuspend the beads.

14. Quickly spin down the tube to collect any sample on the sides of the tube and place the tubes on a magnetic rack. Once the solution is clear, carefully remove and discard the supernatant without disturbing the bead pellet. With a 20 μL pipette tip, carefully remove any residual liquid left at the bottom of the tube without disturbing the beads.

15. Remove the tube from the magnet and add 23 μL 0.1% Tween-20. Vortex briefly to resuspend the beads and quickly spin in a microcentrifuge to collect any sample on the sides of the tube.

16. Place the tube in a thermocycler, with the heated lid on, and run the following program: 3 minutes at 95° C. and hold at 25° C.

17. Remove the tube from the thermocycler, vortex briefly, spin down the contents and place on the magnetic rack.

18. Once the solution is clear, transfer 21 μL of the supernatant into a new tube and discard the beads.

C-F. VDJ Region Amplification and Index Barcode Incorporation

C. T-Cell Receptor Alpha+Beta Chain Enrichment

1. Add the following components to the purified cDNA from previous step 18. Purified cDNA (21 μL), Q5 Reaction Buffer (5×) (10 μL), dNTP mix (1 μL), Q5 Hot Start High-Fidelity DNA Polymerase (1 μL), AbSeq TCR alpha Chain Primer (2 μL), AbSeq TCR beta Chain Primer (2 μL), AbSeq Index Primer (2 μL), and Nuclease-free water (11 μL).
Use only one index primer per PCR reaction.

2. PCR1 cycling conditions:

| CYCLE STEP | TEMP | TIME | CYCLES |
|---|---|---|---|
| Initial Denaturation | 98° C. | 60 seconds | 1 |
| Denaturation | 98° C. | 10 seconds | 12 |
| Annealing | 64° C. | 30 seconds | |
| Extension | 72° C. | 30 seconds | |
| Final Extension | 72° C. | 60 seconds | 1 |
| Hold | 4° C. | ∞ | |

D. AMPure XP Bead Cleanup of PCR Product

1. Vortex AMPure XP beads to resuspend.

2. Add 50 μL of resuspended AMPure XP beads to each 50 μL PCR reactions. Mix well by pipetting or brief vortexing.

3. Incubate for 5 minutes at room temperature.

4. Quickly spin the tube in a microcentrifuge and place it on a magnetic rack. Once the solution is clear (approximately 5 minutes) carefully remove and discard the supernatant without disturbing the bead pellet.

5. Wash beads by adding 200 μL of freshly prepared 80% ethanol to the tube while in the magnetic rack. Incubate at room temperature for 30 seconds, and then carefully remove and discard the supernatant.

6. Repeat Step 5. After supernatant is discarded, use a 20 μL pipette tip to carefully remove any residual liquid left at the bottom of the tube without disturbing the beads.

7. Air dry the beads for 5 minutes with the tube on the magnetic stand and the lid open. Caution: Do not over dry the beads. This may result in lower recovery of DNA target.

8. Elute DNA target from beads by adding 25 μL 0.1% Tween-20 to beads. Mix well on a vortex mixer or by pipetting up and down at least 10 times. Quickly spin the tube and place it on a magnetic rack to separate beads from supernatant.

9. After the solution is clear (about 2 minutes), carefully transfer 25 μL supernatant to a new PCR tube.

E. PCR2 to Enrich Library

1. Mix following components in a sterile nuclease-free tube: Q5 Reaction Buffer (5×) (10 μL), dNTP mix (1 μL), Q5 Hot Start High-Fidelity DNA Polymerase (1 μL), AbSeq PCR2 Primer Mix (4 μL), Purified PCR1 DNA (from previous Step 9) (10 μL), and Nuclease-free water (24 μL)

2. PCR2 cycling conditions:

| CYCLE STEP | TEMP | TIME | CYCLES |
|---|---|---|---|
| Initial Denaturation | 98° C. | 60 seconds | 1 |
| Denaturation | 98° C. | 10 seconds | X* |
| Annealing and Extension | 72° C. | 30 seconds | |
| Hold | 4° C. | ∞ | |

F. Final Library AMPure XP Bead Cleanup

1. Vortex AMPure XP beads to resuspend.

2. Add 37.5 μL of resuspended AMPure XP beads to each 50 μL PCR reaction. Mix well by pipetting or brief vortexing.

3. Incubate for 5 minutes at room temperature.

4. Quickly spin the tube in a microcentrifuge and place it on a magnetic rack. Once the solution is clear (approximately 5 minutes) carefully remove and discard the supernatant without disturbing the bead pellet.

5. Wash beads by adding 200 μL of freshly prepared 80% ethanol to the tube while in the magnetic rack. Incubate at room temperature for 30 seconds, and then carefully remove and discard the supernatant.

6. Repeat Step 5. After supernatant is discarded, carefully remove any residual liquid left at the bottom of the tube without disturbing the beads with a 10 μL pipette tip.

7. Air dry the beads for 5 minutes with the tube on the magnetic stand and the lid open. Do not over dry the beads. This may result in lower recovery of DNA target.

8. Elute DNA target from beads by adding 52 μL 0.1× Tris-EDTA (TE) to beads. Mix well on a vortex mixer or by pipetting up and down at least 10 times.

9. Quickly spin the tube and place it on a magnetic rack to separate beads from supernatant. After the solution is clear (about 2 minutes), carefully transfer 50 μL supernatant to a new PCR tube.

10. Add 37.5 μL of resuspended AMPure XP beads to supernatant. Mix well by pipetting or brief vortexing.
11. Incubate for 5 minutes at room temperature.
12. Quickly spin the tube in a microcentrifuge and place it on a magnetic rack. Once the solution is clear (approximately 5 minutes) carefully remove and discard the supernatant without disturbing the bead pellet.
13. Wash beads by adding 200 μL of freshly prepared 80% ethanol to the tube while in the magnetic rack. Incubate at room temperature for 30 seconds, and then discard the supernatant.
14. Repeat Step 13. After supernatant is discarded, carefully remove any residual liquid left at the bottom of the tube without disturbing the beads with a 10 μL pipette tip.
15. Air dry the beads for 5 minutes while the tube is on the magnetic stand with the lid open. Do not overdry the beads. This may result in lower recovery of DNA target.
16. Elute DNA target from beads by adding 20 μL 0.1× TE to beads. Mix well on a vortex mixer or by pipetting up and down at least 10 times.
17. Quickly spin the tube and place it on a magnetic rack to separate beads from supernatant. After the solution is clear (about 2 minutes), carefully transfer 18 μL supernatant to a new PCR tube.

Figure 3:
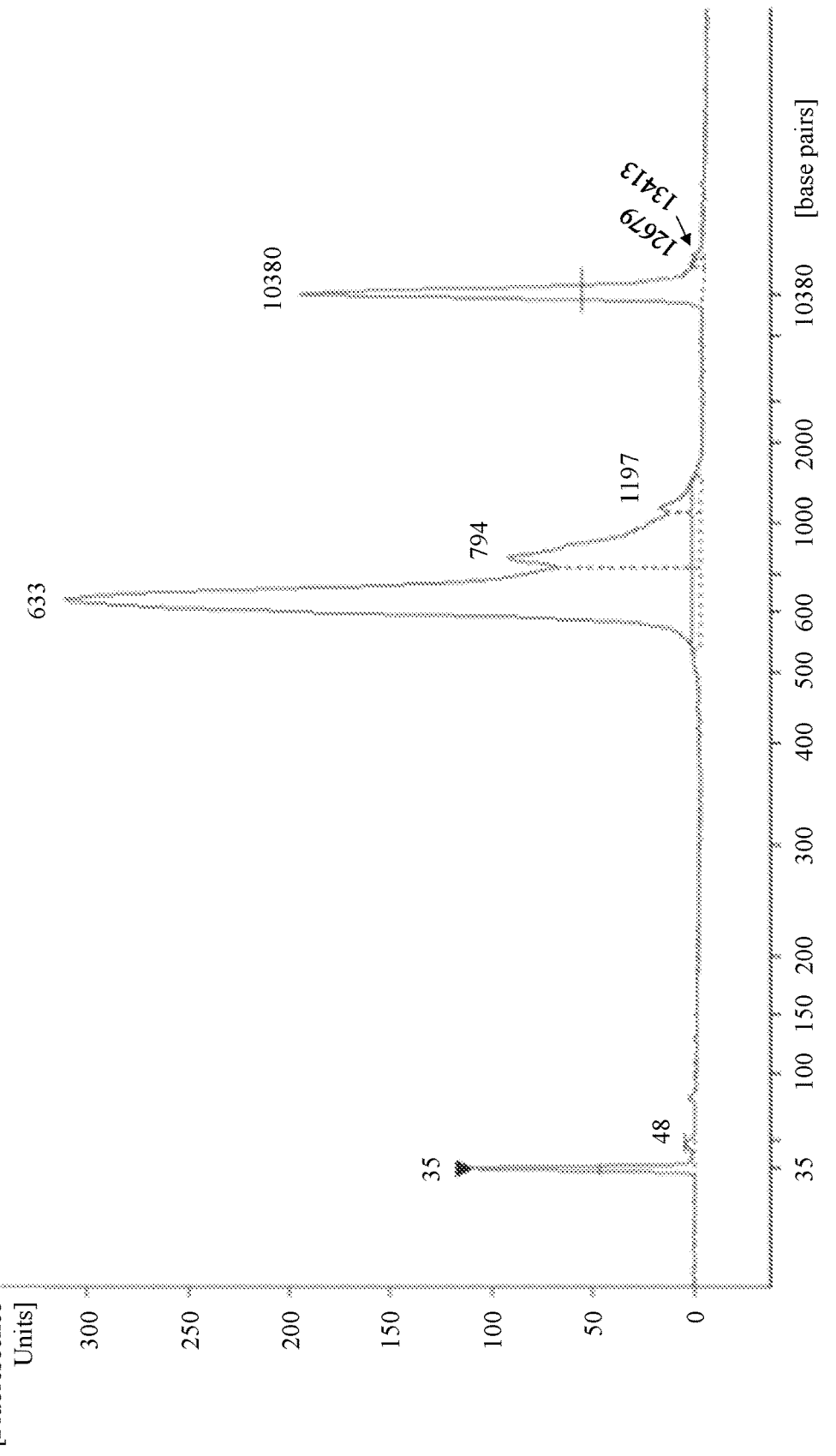
FIG. 3 shows an example of analysis of T cell receptor alpha+beta chain library size distribution on a Bioanalyzer, with the predominant peak at approximately 665 base pairs.

G. Assess Library Quality on a Bioanalyzer® High Sensitivity Chip or TapeStation High Sensitivity D1000 Screen-Tape 1. Dilute library 10-fold in nuclease-free water.
2. Run 1 μL on a DNA High Sensitivity chip
3. Check that the electropherogram shows the expected size distribution. T cell receptor alpha+beta chain libraries will have an average size of approximately 665 base pairs (as shown in FIG. 3).

As described above, RNA was reverse transcribed using a biotinylated oligonucleotide pool and purified with streptavidin beads to create a cDNA pool. VDJ regions from the cDNA in the cDNA pool were amplified by PCR using TCR alpha and beta chain primers and an index primer. CDR3 regions from TCR α/β chains were sequenced by 2× 300 base pair (bp) paired-end sequencing on the MiSeq platform. The sequencing data were analyzed by downstream bioinformatics analysis. The TCR repertoires were analyzed by quantifying the different clonotypes of each patient.

Figure 4:
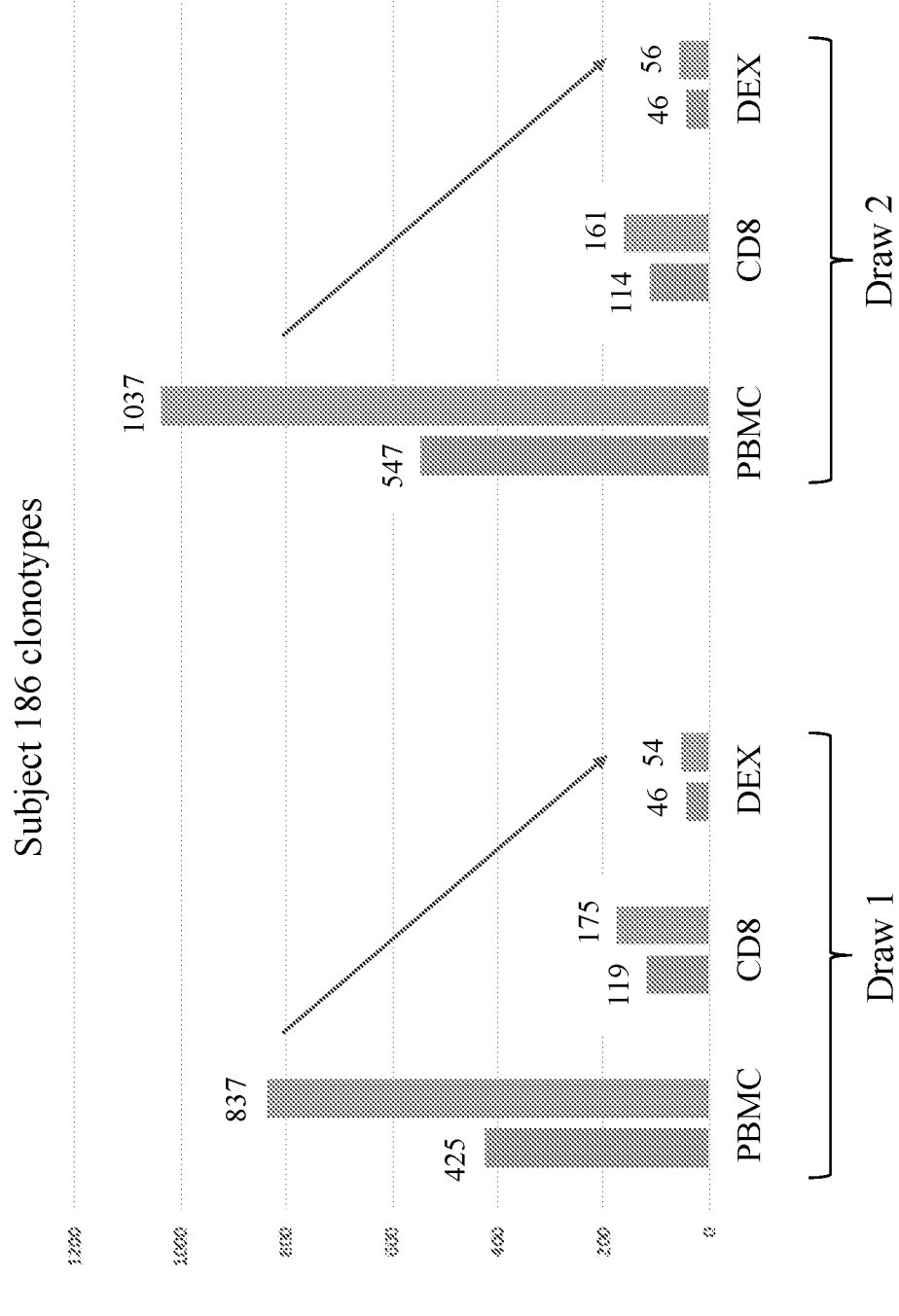
FIG. 4 illustrates a decrease in TCR diversity over two draws.
Figure 5:
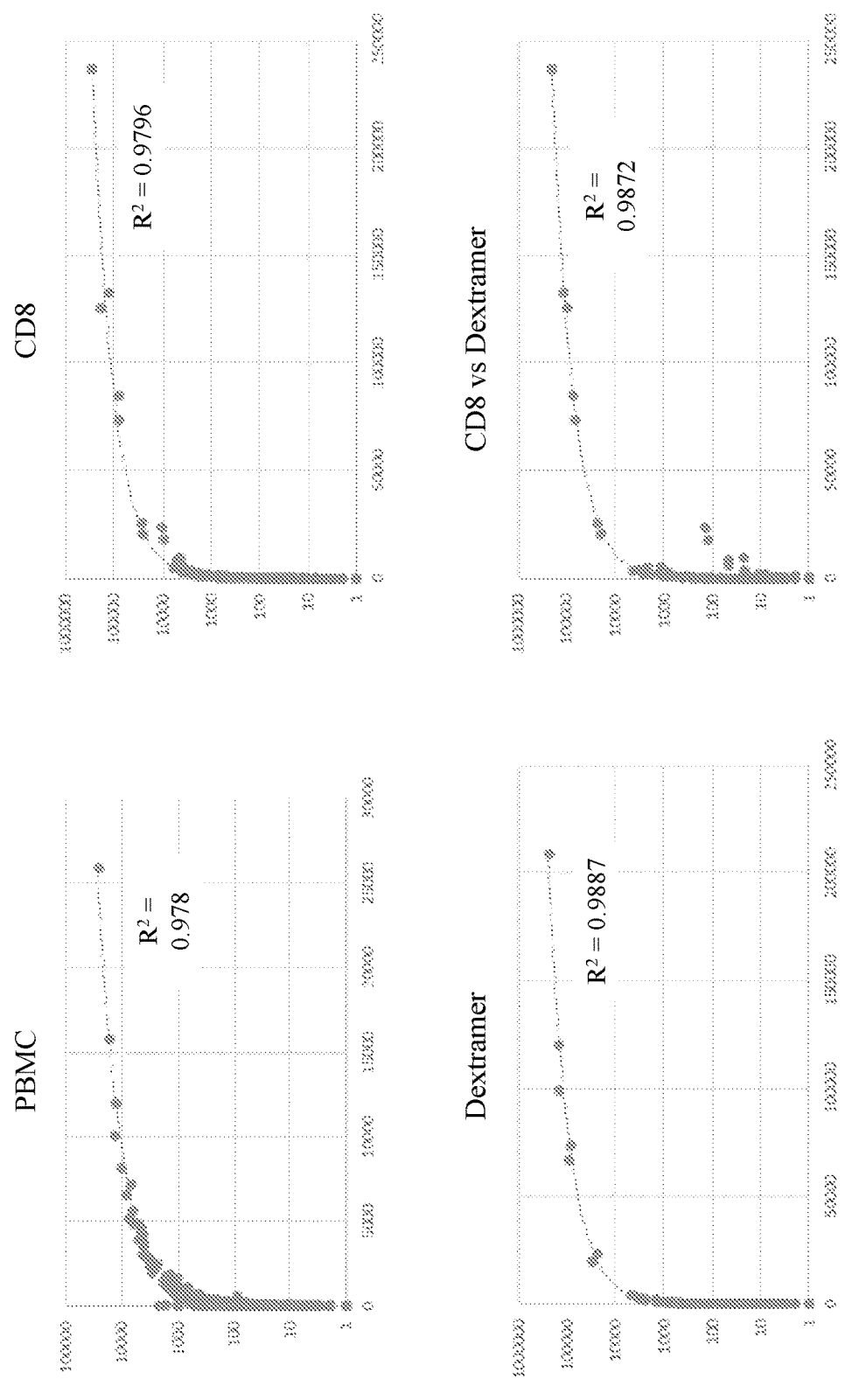
FIG. 5 illustrates the correlations between draw 1 & 2 from FIG. 4.
Figure 6A:
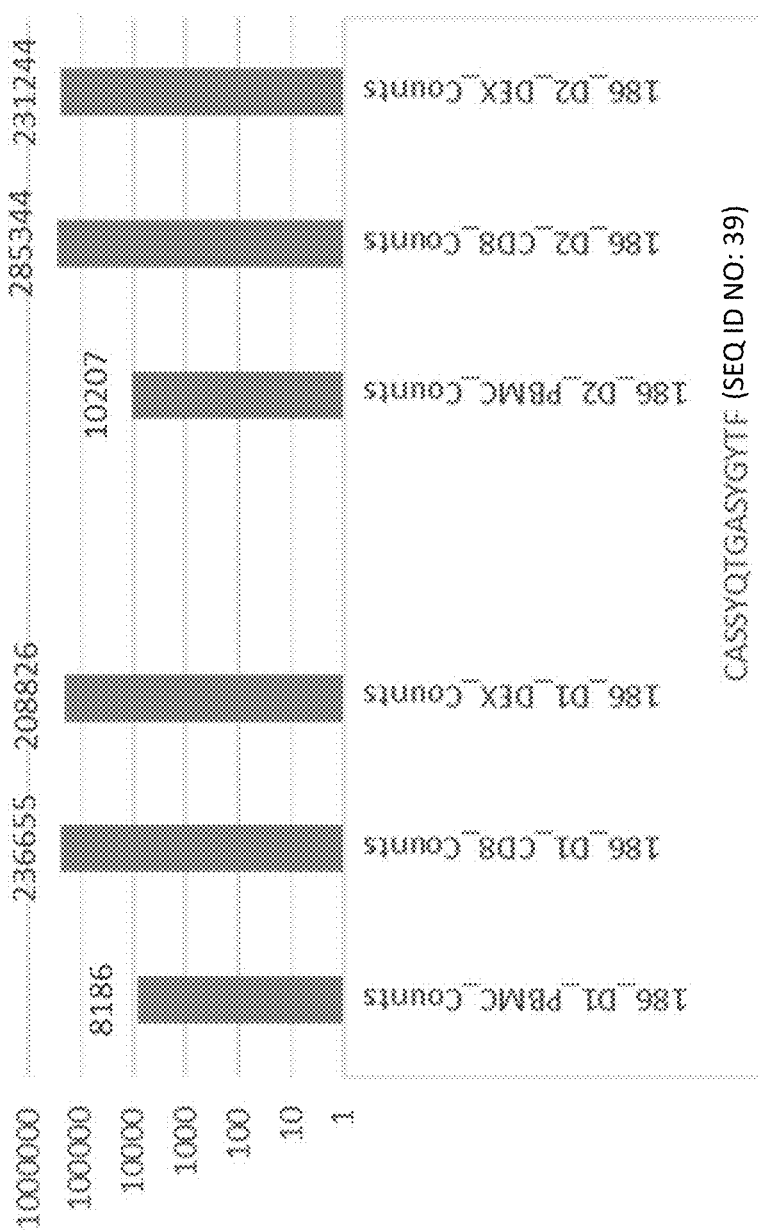
FIGS. 6A, 6B, 6C, and 6D illustrate the evolution of four TCR clonotypes in subject 186.
Figure 6B:
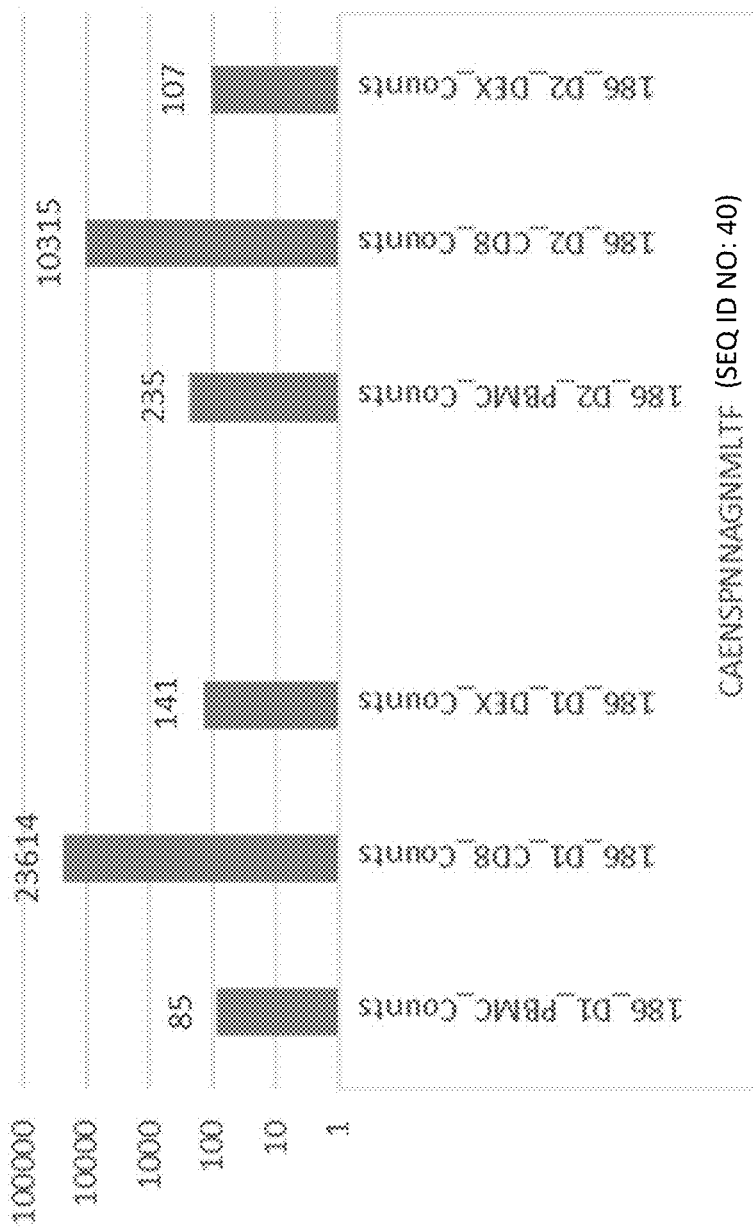
Figure 6C:
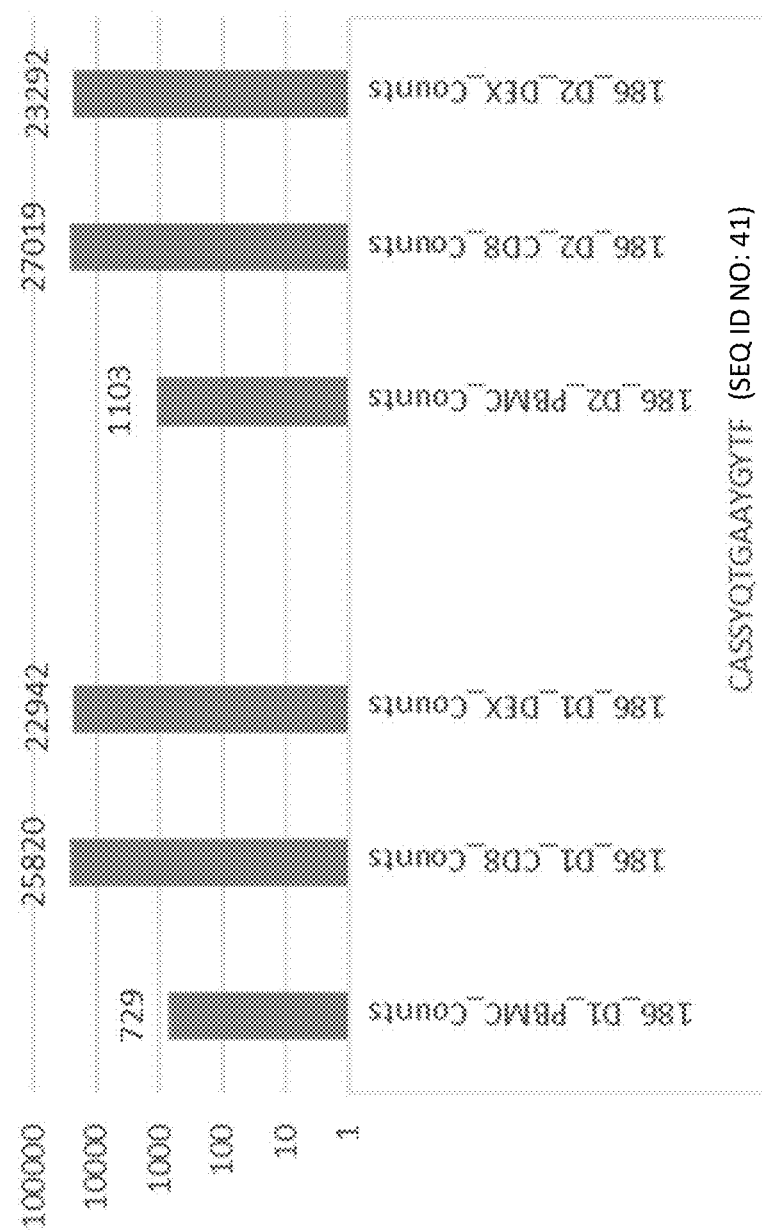
Figure 6D:
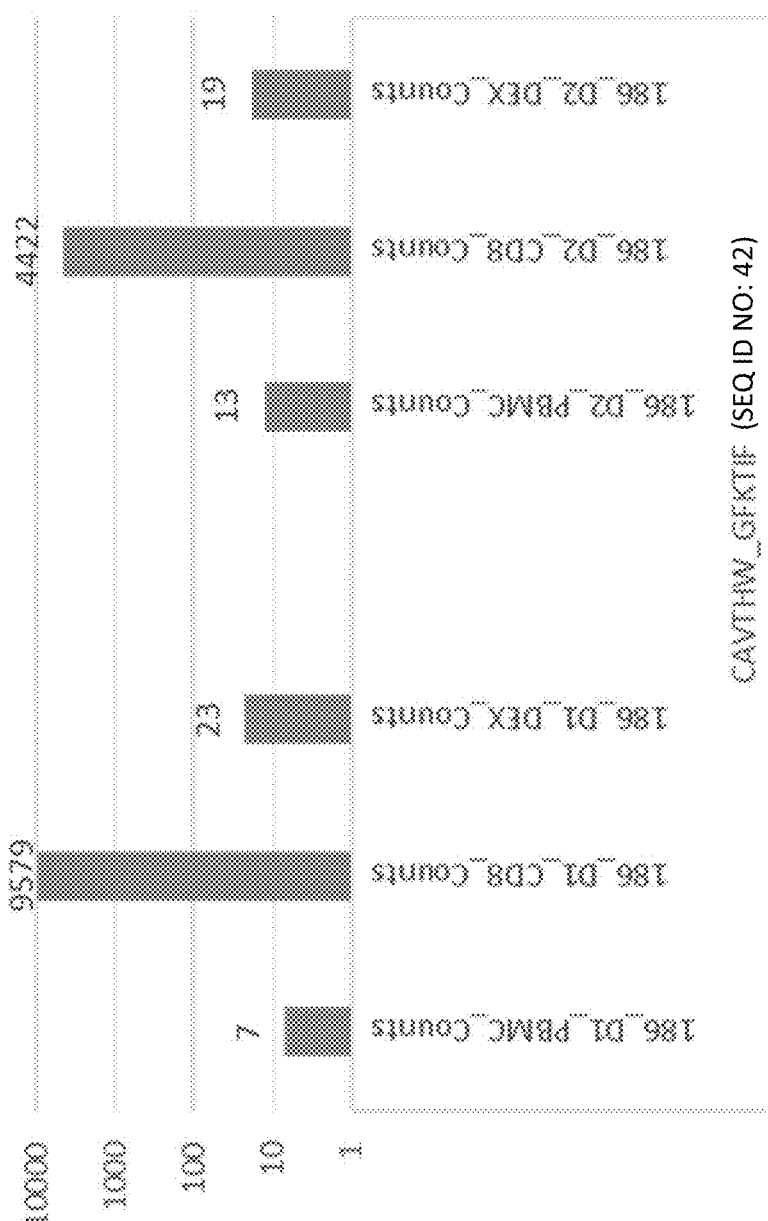

Two healthy subjects were analyzed to establish the efficacy of TCR sequencing (patients #186 & #381). Two blood draws were taken from each subject, with the draws taken six months apart for #186 and 13 months apart for #381. PBMCs isolated from the blood were then incubated with a peptide antigen (NLVPMVATV; (SEQ ID NO: 43)) from human cytomegalovirus pp65. The peptide antigen stimulated cells were split into three groups: total; CD8+ selected; and dextramer enriched. The dextramer binds HLA-A0201. FIGS. 4-6 illustrate TCR sequencing efficacy.

Polyclonal sequencing. FIG. 4 shows that CD8+ selection or dextramer enrichment decreases TCR diversity, as measured by number of CDR3 clonotypes. For each blood draw, RNA reads were quantified for each clonotype isolated from: total PBMCs; CD8+ enriched PBMCs; and dextramer enriched PBMCs. Total clonotypes identified in at least 50 or at least 100 reads were fewer in CD8+ or dextramer enriched cells as compared to total PBMCs.

FIG. 5 shows a strong correlation between draw 1 and draw 2 individual clonotype levels. Clonotypes at draw 1 strongly correlate with the levels of the same clonotypes at draw 2. Clonotype read numbers were plotted for each of the indicated variables. Draws 1 & 2 were compared for total PBMCs, CD8+ PBMCs, and dextramer enriched PBMCs. All showed strong correlations, as demonstrated by the $R^2$ value for each best fit curve. Furthermore, clonotype levels at draw 1 for CD8+PBMCs correlate with the levels of the same in dextramer enriched PBMCs. This demonstrates the reproducibility of the TCR sequencing and that CD8+ and dextramer enrichment yield similar results.

FIGS. 6A, 6B, 6C, and 6D show comparison of non-enriched, CD8-enriched, and dextramer-enriched reads.

Single cell sequencing. PBMCs were isolated from a healthy subject and incubated with the pp65 peptide. Peptide stimulated cells were then CD8+ selected or dextramer enriched using a dextramer against HLA-A0201.

Single PBMCs, reverse transcription (RT) reagents, gel beads with 10× barcoded oligonucleotides, and oil were combined to form single cell gel beads in emulsion. Reverse transcription and second strand synthesis preceded cDNA amplification. Target amplification produced sequencing libraries for TCR profiling. Gene expression sequencing libraries were also produced for mRNA sequencing of single cells. Sequencing libraries were then sequenced and the sequences analyzed.

Figure 7:
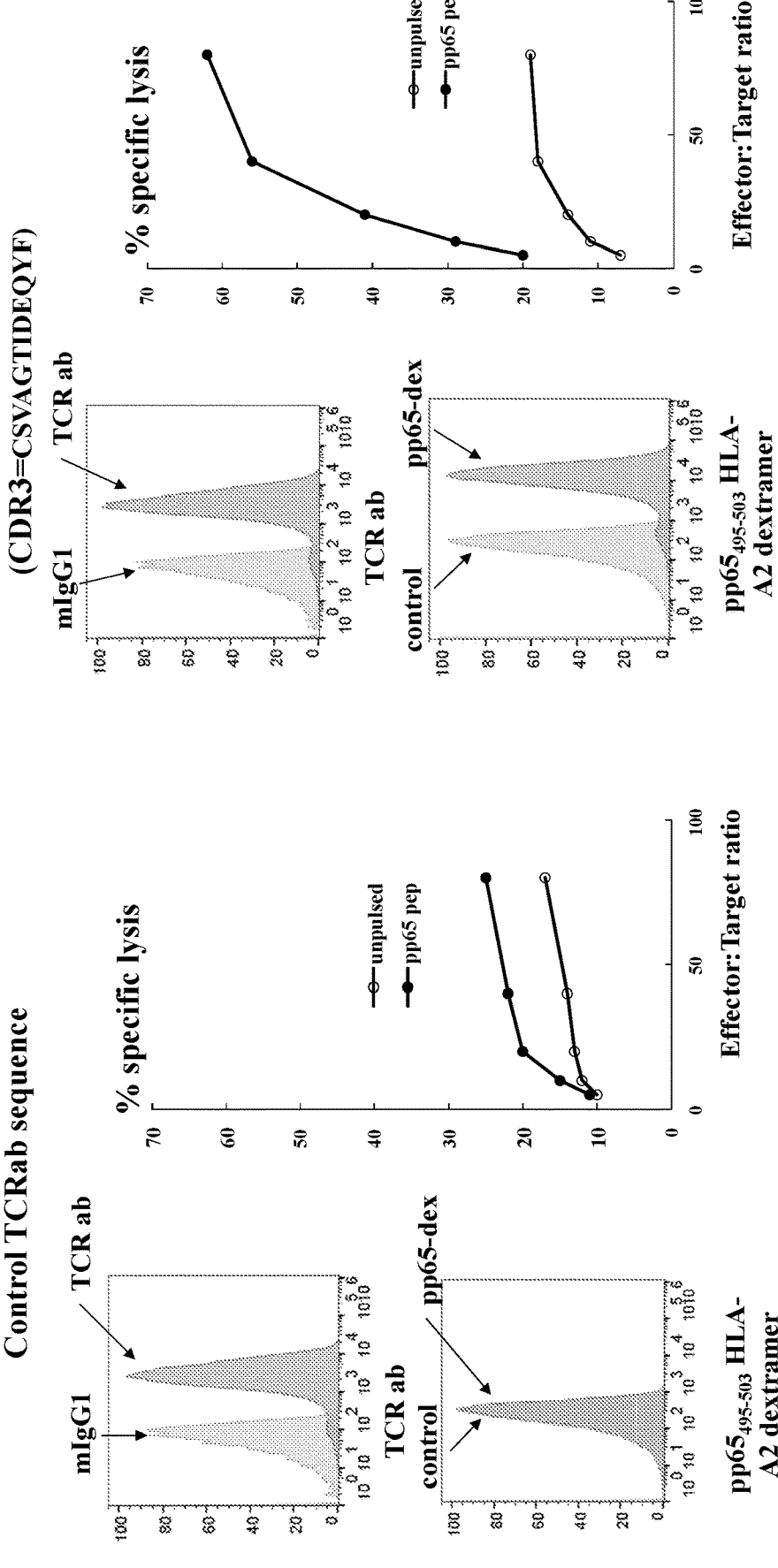
FIG. 7 shows TCR expression and function in haNK cells.

Tables 4, 5, & 6 show the identification and quantification of individual clonotypes from single cells. Table 4 shows the clonotypes, along with their number of times read (frequency) and proportion of total reads, for a cell selected from total PBMCs. Tables 5 & 6 show the same for CD8+ and dextramer enriched cells, respectively. Tables 5 & 6 further illustrate, in the far right column of each table, that single cells selected from the CD8+ population or dextramer enriched population contain similar highly expressed clonotypes to the highly expressed clonotypes of those populations in the polyclonal total PBMC samples shown in Table 4. FIG. 7 shows that cells expressing pp65-reactive TCRαβ (CDR3-CSVAGTIDEQYF (SEQ ID NO:1)) promote effective lysis.

TABLE 4

Subject #381 PBMCs single cell data

| ID | | CDR3s | Frequency | Proportion |
|---|---|---|---|---|
| clonotype1 | TRA: | CAGDSGGTSYGKLTF (SEQ ID NO: 2) | 33 | 1.10% |
| | TRB: | CSVVSVESYEQYF (SEQ ID NO: 3) | | |
| clonotype2 | TRA: | CATEGGTSYGKLTF (SEQ ID NO: 4) | 24 | 0.80% |
| | TRB: | CSALGTDSYEQYF (SEQ ID NO: 5) | | |
| clonotype3 | TRA: | CVVSSYNNDMRF (SEQ ID NO: 6) | 18 | 0.60% |
| | TRB: | CASSSTGGALYEQYF (SEQ ID NO: 7) | | |
| clonotype4 | TRA: | CALAAGGTSYGKLTF (SEQ ID NO: 8) | 18 | 0.60% |
| | TRB: | CASSGAYPEAFF (SEQ ID NO: 9) | | |
| clonotype5 | TRA: | CAPMNRDDKIIF (SEQ ID NO: 10) | 17 | 0.60% |
| | TRB: | CASSHLGYEQYF (SEQ ID NO: 11) | | |

TABLE 4-continued

| | | | Pro- |
|---|---|---|---|
| | Subject #381 PBMCs single cell data | | |
| ID | CDR3s | Frequency | portion |
| clonotype6 | TRA: CAVNPYNTDKLIF (SEQ ID NO: 12) TRB: CSARDLGTEEAFF (SEQ ID NO: 13) | 15 | 0.50% |
| clonotype7 | TRA: CVVSLRITGGGNKLTF (SEQ ID NO: 14) TRB: CASSLSFGGFYNEQFF (SEQ ID NO: 15) | 13 | 0.40% |
| clonotype9 | TRB: CASSHLGYEQYF (SEQ ID NO: 16) | 12 | 0.40% |

TABLE 4-continued

| | | | Pro- |
|---|---|---|---|
| | Subject #381 PBMCs single cell data | | |
| ID | CDR3s | Frequency | portion |
| clonotype8 | TRA: CAASGRNYGQNFVF (SEQ ID NO: 17) TRA: CLRGCRMDSNYQLIW (SEQ ID NO: 18) TRB: CSGIGVESYEQYF (SEQ ID NO: 19) | 12 | 0.40% |
| clonotype11 | TRA: CAVSSSNNLFF (SEQ ID NO: 20) TRB: CASSSLTGAGDTIYF (SEQ ID NO: 21) | 11 | 0.40% |

TABLE 5

| | | | | | polyclonal |
|---|---|---|---|---|---|
| | Subject #381 CD8+ selection | | | | |
| ID | CDR3s | Freq'y. | Prop'n. | Comments | CD8 |
| clonotype1 | TRA: CVVSLRITGGGNKLTF (SEQ ID NO: 14) TRB: CASSLSFGGFYNEQFF (SEQ ID NO: 15) | 1,386 | 20.90% | no. 3 in DEX | No. 1 No. 2 |
| clonotype2 | TRA: CAFMNHLSLNAGKSTF (SEQ ID NO: 22) TRB: CASSYGAYEQYF (SEQ ID NO: 23) | 879 | 13.30% | no. 5 in DEX | No. 4 No. 3 |
| clonotype3 | TRA: CAMREGTDSSYKLIF (SEQ ID NO: 24) TRB: CASSNHEEWGAASPLHF (SEQ ID NO: 25) | 408 | 6.20% | no. 10 in DEX | No. 6 No. 5 |
| clonotype4 | TRA: CALATGGGADGLTF (SEQ ID NO: 26) TRB: CASSLEPGTDLLGYGYTF (SEQ ID NO: 27) | 307 | 4.60% | no. 8 in DEX | No. 9 No. 11 |
| clonotype5 | TRA: CAFMNHLSLNAGKSTF (SEQ ID NO: 22) | 293 | 4.40% | | No. 4 |
| clonotype6 | TRA: CVVSLRITGGGNKLTF (SEQ ID NO: 14) TRA: CAMREGTDSSYKLIF (SEQ ID NO: 24) | 226 | 3.40% | | No. 1 No. 6 |
| clonotype7 | TRA: CAVVSRGGTASKLTF (SEQ ID NO: 28) TRB: CASSNHEEWGAASPLHF (SEQ ID NO: 25) | 183 | 2.80% | no.6 in DEX | No. 14 No. 5 |
| clonotype8 | TRA: CAGVARKAAGNKLTF (SEQ ID NO: 29) TRB: CASSLSPSTGNYGYTF (SEQ ID NO: 30) | 149 | 2.30% | | No. 7 No. 15 |
| clonotype9 | TRB: CASSYGAYEQYF (SEQ ID NO: 23) | 137 | 2.10% | | No. 3 |
| clonotype10 | TRA: CAVPTGFQKLVF (SEQ ID NO: 31) TRB: CASSEGLGNSPLHF (SEQ ID NO: 32) | 127 | 1.90% | | No. 12 No. 22 |

TABLE 6

Subject #381 DEX data

| ID | | CDR3s | Freq'y. | Prop'n. | Comments | polyclonal DEX |
|---|---|---|---|---|---|---|
| clonotype1 | TRA: | CAVNVPLSYQLTF (SEQ ID NO: 33) | 95 | 19.30% | | No. 4 |
| | TRB: | CSVAGTIDEQYF (SEQ ID NO: 1) | | | | No. 1 |
| clonotype2 | TRA: | CALSEAGAGSYQLTF (SEQ ID NO: 34) | 67 | 13.60% | | No. 5 |
| | TRB: | CASSQEPVASFFVEQFF (SEQ ID NO: 35) | | | | No. 2 |
| clonotype3 | TRA: | CVVSLRITGGGNKLTF (SEQ ID NO: 14) | 46 | 9.30% | no. 1 in CD8 | No. 6 |
| | TRB: | CASSLSFGGFYNEQFF (SEQ ID NO: 15) | | | | No. 10 |
| clonotype4 | TRA: | CITSGTYKYIF (SEQ ID NO: 36) | 41 | 8.30% | | No. 3 |
| | TRB: | CASSLSDTGLVDYEQYF (SEQ ID NO: 37) | | | | No. 8 |
| clonotype5 | TRA: | CAFMNHLSLNAGKSTF (SEQ ID NO: 22) | 33 | 6.70% | no. 2 in CD8 | No. 17 |
| | TRB: | CASSYGAYEQYF (SEQ ID NO: 23) | | | | No. 13 |
| clonotype6 | TRA: | CAMREGTDSSYKLIF (SEQ ID NO: 24) | 16 | 3.30% | no. 7 in CD8 | No. 21 |
| | TRA: | CAVVSRGGTASKLTF (SEQ ID NO: 28) | | | | No. 14 |
| | TRB: | CASSNHEEWGAASPLHF (SEQ ID NO: 25) | | | | No. 16 |
| clonotype7 | TRB: | CASSLLTGFGTEAFF (SEQ ID NO: 38) | 15 | 3.00% | | No. 7 |
| clonotype9 | TRB: | CSVAGTIDEQYF (SEQ ID NO: 1) | 10 | 2.00% | | No. 1 |
| clonotype8 | TRA: | CALATGGGADGLTF (SEQ ID NO: 26) | 10 | 2.00% | no. 4 in CD8 | No. 18 |
| | TRB: | CASSLEPGTDLLGYGYTF (SEQ ID NO: 27) | | | | No. 11 |
| clonotype10 | TRA: | CAMREGTDSSYKLIF (SEQ ID NO: 24) | 10 | 2.00% | no. 3 in CD8 | No. 21 |
| | TRB: | CASSNHEEWGAASPLHF (SEQ ID NO: 25) | | | | No. 16 |

Figure 8:
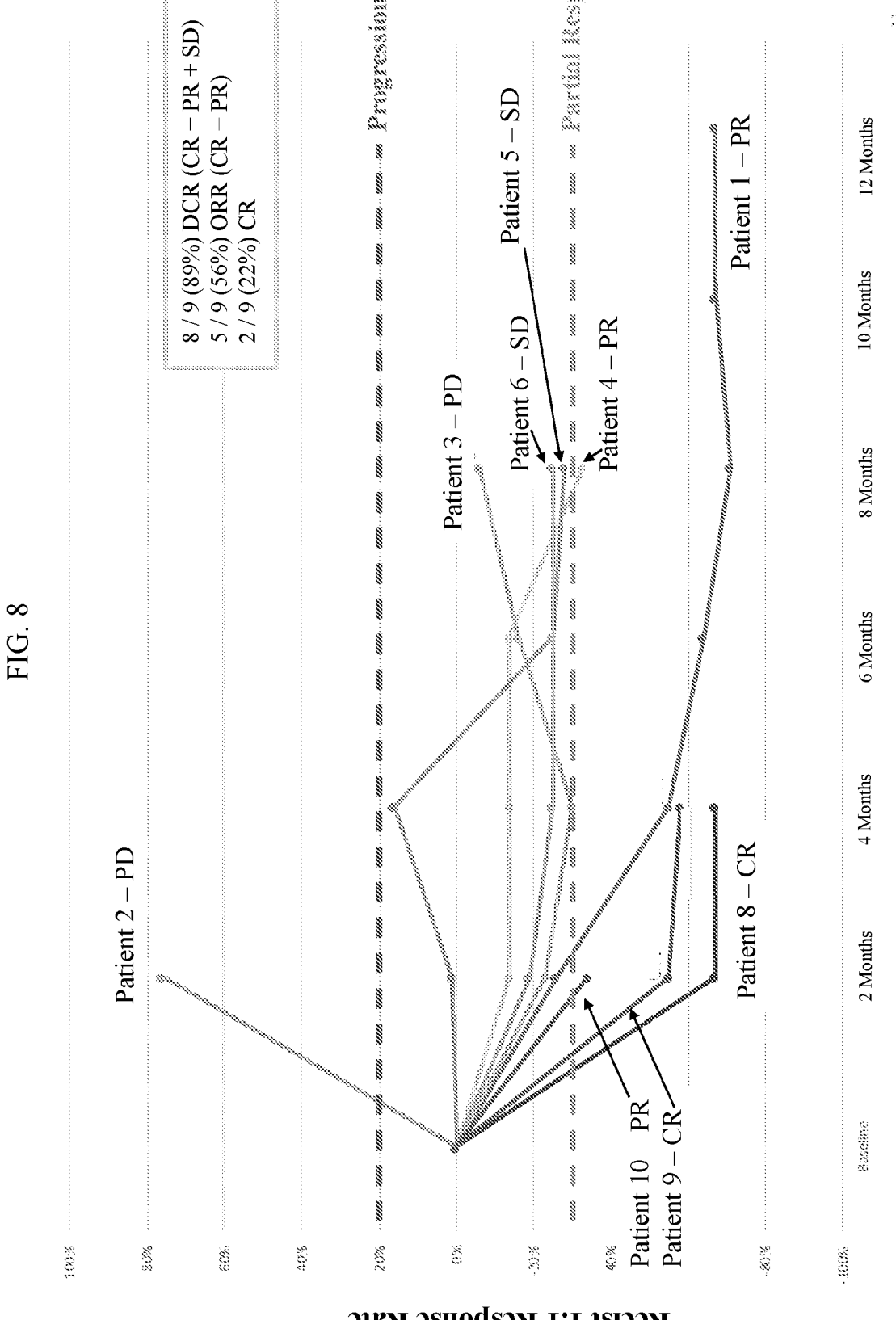
FIG. 8 illustrates the success or failure of therapy over time in the nine relapsed TNBC patients.

Example 4. TCR Repertoires as Prognostic Indicators in TNBC. TCR diversity in response to treatment of TNBC patients was analyzed. Patients were treated with low-dose metronomic Nab-paclitaxel and low-dose immune-modulators (5-FU/L, Cytoxan, cisplatin, and bevacizumab) at days 1~4 and 15, adenovirus-based therapies (Ad-CEA, Ad-MUC1, Ad-Brachyury, and Ad-HER2) and yeast-based therapies (Ye-CEA, Ye-RAS, and Ye-Brachyury) at day 5, N-803 and avelumab at day 9, and NK CD16 targeted haNK at days 9, 11, and 16. The TCR repertoire was analyzed at treatment initiation and at approximately two month intervals thereafter. FIG. 8 shows the Recist 1.1 response rate for each patient. The patient identification numbers for each patient are shown at the bottom of the figure, and those same patient identification numbers are also used for patient identification in Table 7 below.

Table 7 shows results of analyses of the TCR repertoire at treatment initiation and at approximately two month intervals thereafter, for months 2 to 10. The TCR repertoire was quantified as the Shannon-Weiner Index, the fold-change of which is shown for each time point under the corresponding column. The irRC and Recist 1.1 measurements are shown for each time point under the corresponding column, along with the percent change for each measure.

In patients with CR (Complete Response) or PR (Partial Response), PBMC analysis revealed that patients with CR or PR frequently showed >13x increase in TCR diversity (Shannon-Weiner Diversity Index, SWDI) 2 months after treatment initiation & increased SWDI thereafter (e.g. Patient 8); conversely, in patients with SD (Stable Disease) or PD (Progressive Disease), PBMC TCR diversity increased <2x (e.g. Patient 3) or decreased.

TABLE 7

TCR repertoire, patient response, and disease progression analyses in TNBC

| Patient Number | Response | Measure | Base-line | Month 2 | Month 4 | Month 6 | Month 8 | Month 10 |
|---|---|---|---|---|---|---|---|---|
| 1 | Partial Response | SW | 74 | 1177 | 238 | 3516 | 947 | 492 |
| | | fold-SW | | 15.90 | 3.22 | 47.51 | 12.80 | 6.65 |
| | | irRC | 3209 | 860 | 291 | 227 | 129 | 139 |
| | | irRC % | | −73% | −91% | −93% | −96% | −96% |
| | | Recist1.1 | 58 | 43 | 26 | 21 | 17 | 19 |
| | | Recist % | | −26% | −55% | −64% | −71% | −67% |
| 3 | Progressive Disease | SW | 2489 | 1513 | 724 | 2502 | 3793 | |
| | | fold-SW | | 0.61 | 0.29 | 1.01 | 1.52 | |
| | | irRC | 3006 | 1172 | 1245 | 2182 | 2786 | |
| | | irRC % | | −61% | −58% | −27% | −7% | |
| | | Recist1.1 | 113 | 87 | 80 | 95 | 106 | |
| | | Recist % | | −23% | −29% | −16% | −6% | |
| 4 | Partial Response | SW | 3576 | 6655 | 3300 | 1990 | 6427 | 1754 |
| | | fold-SW | | 1.86 | 0.92 | 0.56 | 1.80 | 0.49 |
| | | irRC | 366 | 286 | 286 | * | *** | *** |
| | | irRC % | | −22% | −22% | * | *** | *** |
| | | Recist1.1 | 21 | 18 | 18 | * | *** | ** |
| | | Recist % | | −14% | −14% | * | *** | ** |
| 5 | Stable Disease | SW | 11553 | 2388 | 10808 | 5775 | 1342 | 3258 |
| | | fold-SW | | 0.21 | 0.94 | 0.50 | 0.12 | 0.28 |
| | | irRC | 6429 | 6919 | 8478 | *** | *** | *** |
| | | irRC % | | 8% | 32% | *** | *** | *** |
| | | Recist1.1 | 134 | 135 | 156 | *** | *** | *** |
| | | Recist % | | 1% | 16% | *** | *** | *** |
| 6 | Stable Disease | SW | 649 | 797 | 2614 | 43 | 1972 | 1749 |
| | | fold-SW | | 1.23 | 4.02 | 0.07 | 3.03 | 2.69 |
| | | irRC | 512 | 272 | 240 | *** | *** | *** |
| | | irRC % | | 47% | 53% | *** | *** | *** |
| | | Recist1.1 | 32 | 26 | 26 | *** | *** | *** |
| | | Recist % | | 19% | 19% | *** | *** | *** |
| 8 | Complete Response | SW | 31 | 419 | 512 | 1001 | 58 | |
| | | fold-SW | | 13.52 | 16.52 | 32.29 | 1.87 | |
| | | irRC | 315 | 30 | *** | *** | *** | *** |
| | | irRC % | | −90% | *** | *** | *** | *** |
| | | Recist1.1 | 15 | 5 | *** | *** | *** | *** |
| | | Recist % | | −67% | *** | *** | *** | *** |

Example 5. TCR Repertoires as Prognostic Indicators in Pancreatic Cancer. The T cell receptor (TCR) diversity in response to treatment of pancreatic cancer patients was analyzed in patients undergoing the multimodal cancer immunotherapy study treatment of FIG. 9. The TCR repertoire was analyzed at treatment initiation and at approximately two month intervals thereafter.

Table 8 shows the results of analyses of the TCR repertoire at treatment initiation and at approximately two month intervals thereafter, for months 2 to 10. The TCR repertoire was quantified as the Shannon-Weiner Index, the fold-change of which is shown for each time point under the corresponding column. The irRC and Recist 1.1 measurements are shown for each time point under the corresponding column, along with the percent change for each measure.

TABLE 8

TCR repertoire, patient response, and disease progression analyses in pancreatic cancer

| Patient Number | Response | Measure | Base-line | Month 2 | Month 4 | Month 6 | Month 8 | Month 10 |
|---|---|---|---|---|---|---|---|---|
| PC1 | ? | SW | 3563 | 1193 | 789 | 662 | 816 | 1108 |
| | | fold-SW | | 0.33 | 0.22 | 0.19 | 0.22 | 0.31 |
| | | irRC | 3027 | 2388 | 2047 | 2422 | 3259 | 2911 |
| | | irRC % | | −21% | −32% | −20% | 8% | −4% |
| | | Recist1.1 | 110 | 97 | 88 | 102 | 119 | 116 |
| | | Recist % | | −12% | −20% | −7% | 8% | 5% |

TABLE 8-continued

| Patient Number | Response | Measure | Base-line | Month 2 | Month 4 | Month 6 | Month 8 | Month 10 |
|---|---|---|---|---|---|---|---|---|
| | | | TCR repertoire, patient response, and disease progression analyses in pancreatic cancer | | | | | |
| PC4 | ? | SW | 131 | 84 | 135 | 66 | | |
| | | fold-SW | | 0.64 | 1.03 | 0.50 | | |
| | | irRC | 1948 | 1941 | 2205 | 2970 | | |
| | | irRC % | | 0% | 13% | 52% | | |
| | | Recist1.1 | 81 | 86 | 91 | 128 | | |
| | | Recist % | | 6% | 12% | 58% | | |

Example 6. Ig chain analyses. Table 9 shows the results of analyses of the repertoire of Ig kappa chains, lambda chains, and heavy chains, respectively, for patient T671/3.067-001-001 (Patient 1, achieved Partial Response) of the TNBC study. The results are shown for the indicated Ig chain repertoire at treatment initiation and at approximately two month intervals thereafter, for months 2 to 10. The Ig chain repertoires were quantified as the Shannon-Weiner Index, the fold-change of which is shown for each time point under the corresponding column. The irRC and Recist 1.1 measurements are shown for each time point under the corresponding column, along with the percent change for each measure.

TABLE 9

| | Measure | Base-line | Month 2 | Month 4 | Month 6 | Month 8 | Month 10 |
|---|---|---|---|---|---|---|---|
| | | IgG lambda, kappa, and heavy chain analsyes and disease progression analyses | | | | | |
| Kappa | SW | 6.4 | 3.19 | 2.95 | 5.02 | 3.54 | 4.91 |
| chain | fold-SW | | 0.50 | 0.46 | 0.78 | 0.55 | 0.77 |
| Lambda | SW | 5.32 | 3.02 | 2.31 | 3.78 | 3.39 | 3.98 |
| chain | fold-SW | | 0.57 | 0.43 | 0.71 | 0.64 | 0.75 |
| Heavy | SW | 3.02 | 3.07 | 0.99 | 2.33 | 2.8 | 4.57 |
| chain | fold-SW | | 1.02 | 0.32 | 0.77 | 0.93 | 1.51 |
| irRC | irRC | 3209 | 860 | 291 | 227 | 129 | 139 |
| | irRC % | | −34% | −78% | −83% | −90% | −89% |
| Recist1.1 | Recist1.1 | 58 | 43 | 26 | 21 | 17 | 19 |
| | Recist % | | −26% | −55% | −64% | −71% | −67% |

Example 7. Syngeneic murine model to identify T cells with anti-tumor activity. Syngeneic murine models involve the injection of immunologically compatible cancer cells into immunocompetent mice. The Lewis Lung Carcinoma (LLC) model is the only reproducible syngeneic mice model for lung cancer. LLC tumor bearing mice treated with N-803/PD1 combination therapy have increased infiltration of both T and NK cells in the tumor. Amplified necrosis is observed in the combination therapy in comparison to the monotherapy alone. Clonal analysis of the T cell population via TCR repertoire sequencing helps to identify T cells with anti-tumor activity.

An experiment is conducted as follows:
1 million LLC-A9F1 (a subclone of LLC) tumors are injected into C57BL/6 female mice
The mice are treated subcutaneously approximately 3 weeks later with N-803 (Lot No. 09012016), Anti-PD1 mAb (Bioxcell, RMP1-14 clone, BE0146 Catalog No., Lot No. 640517F1), or both.
Each cage has 4 to 5 mice and 1 mouse of each condition in each cage.
Treatment is on day 1, day 3 and day 6. Mice are sacrificed on Day 7.

Blood is collected on Day 1 before treatment and Day 7 before sacrificing.
Mouse α/β TCR chains sequencing libraries are generated and sequenced on a MiSeq platform.
Analyses of the TCR repertoire, as described herein, are performed to determine TCR diversity and identify T cells that have anti-tumor activity. The results will show that mice receiving combination therapy and having greater TCR diversity respond better to the treatment. The results will also identify TCRs with anti-tumor activity that can be used, for example, to develop novel therapeutic treatments.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

Unless otherwise specified, it is to be understood that each embodiment may be used alone or in combination with any one or more other embodiments.

Variations, modifications, and other implementations of what is described herein will occur to those of ordinary skill, and the preceding illustrative description is not intended to be limiting.

Each of the described embodiments may be combined individually or in combination with one or more other embodiments.

Those skilled in the art will recognize or be able to ascertain using no more than routine experimentation, numerous equivalents to the compounds, compositions, and methods of use thereof described herein. Such equivalents are considered to be within the scope of the disclosure.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

---

What is claimed is:

1. A method of treating cancer in a patient who has been receiving a multimodal cancer immunotherapy for at least two months, the method comprising:
   a. calculating T cell receptor (TCR) diversity in a blood sample from the cancer patient before initiation of the multimodal cancer immunotherapy, or at initiation of the multimodal cancer immunotherapy;
   b. calculating the TCR diversity in a blood sample from the cancer patient at least two months after initiation of the multimodal cancer immunotherapy to the patient;
   c. comparing the TCR diversity from steps a and b; and
   d. continuing administration of the multimodal cancer immunotherapy to the patient, if the T cell receptor (TCR) diversity in the blood sample from the patient increases at least three-fold between steps a and b;
   wherein
   the multimodal cancer immunotherapy comprises an NK cell selected from the group consisting of aNK, haNK, taNK, and t-haNK; or
   the multimodal cancer immunotherapy comprises two or more immunotherapies selected from the group consisting of a viral vector expressing an antigen, a yeast immunotherapy, an immune checkpoint inhibitor, and an IL-15 superagonist.

2. The method of claim 1, wherein the multimodal cancer immunotherapy further comprises an immunotherapy selected from the group consisting of aldoxorubicin, N-803, ETBX-011, ETBX-051, ETBX-061, GI-4000, GI-6207, GI-6301, NK cells, avelumab, bevacizumab, capecitabine, cisplatin, cyclophosphamide, 5-fluorouracil, leucovorin, and nab-paclitaxel.

3. The method of claim 1, wherein the patient is administered at least one cancer therapy that is not an immunotherapy.

4. The method of claim 1, wherein the cancer is selected from the group consisting of lung cancer, skin cancer, brain cancer, spinal cord cancer, breast cancer, colon cancer, rectal cancer, liver cancer, pancreatic cancer, head and neck cancer, gall bladder cancer, ovarian cancer, urothelial cancer, and blood cancer.

5. The method of claim 1, wherein the cancer is selected from the group consisting of non-small-cell lung carcinoma (NSCLC), triple negative breast cancer (TNBC), head & neck squamous cell carcinoma (HNSCC), pancreatic adeno-carcinoma, chordoma, melanoma, Merkel cell carcinoma, non-Hodgkin lymphoma, acute myelogenous leukemia, myelodysplastic syndrome, neuroblastoma, and glioblastoma.

6. The method of claim 1, wherein the TCR diversity is calculated as a Shannon Wiener diversity index.

7. The method of claim 1, wherein the TCR diversity is calculated for CDR3 regions from TCR $\alpha/\beta$ chains.

8. The method of claim 1, wherein the TCR diversity is calculated for RNA sequences encoding CDR3 regions from TCR $\alpha/\beta$ chains.

9. The method of claim 1, further comprising administering to the patient a cancer therapy selected from the group consisting of stereotactic body radiation therapy (SBRT), a low dose chemotherapy, and a low dose radiation therapy.

* * * * *

SEQUENCE LISTING

```
<160> NUMBER OF SEQ ID NOS: 43

<210> SEQ ID NO 1
<211> LENGTH: 12
<212> TYPE: PRT
<213> ORGANISM: Artificial Sequence
<220> FEATURE:
<223> OTHER INFORMATION: synthetic

<400> SEQUENCE: 1

Cys Ser Val Ala Gly Thr Ile Asp Glu Gln Tyr Phe
1               5                   10

<210> SEQ ID NO 2
<211> LENGTH: 15
<212> TYPE: PRT
<213> ORGANISM: Artificial Sequence
<220> FEATURE:
<223> OTHER INFORMATION: synthetic

<400> SEQUENCE: 2

Cys Ala Gly Asp Ser Gly Gly Thr Ser Tyr Gly Lys Leu Thr Phe
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: synthetic

<400> SEQUENCE: 3

Cys Ser Val Val Ser Val Glu Ser Tyr Glu Gln Tyr Phe
1               5                   10

<210> SEQ ID NO 4
<211> LENGTH: 14
<212> TYPE: PRT
<213> ORGANISM: Artificial Sequence
<220> FEATURE:
<223> OTHER INFORMATION: synthetic

<400> SEQUENCE: 4

Cys Ala Thr Glu Gly Gly Thr Ser Tyr Gly Lys Leu Thr Phe
1               5                   10

<210> SEQ ID NO 5
<211> LENGTH: 13
<212> TYPE: PRT
<213> ORGANISM: Artificial Sequence
<220> FEATURE:
<223> OTHER INFORMATION: synthetic

<400> SEQUENCE: 5

Cys Ser Ala Leu Gly Thr Asp Ser Tyr Glu Gln Tyr Phe
1               5                   10
```

```
<210> SEQ ID NO 6
<211> LENGTH: 12
<212> TYPE: PRT
<213> ORGANISM: Artificial Sequence
<220> FEATURE:
<223> OTHER INFORMATION: synthetic

<400> SEQUENCE: 6

Cys Val Val Ser Ser Tyr Asn Asn Asp Met Arg Phe
1               5                   10

<210> SEQ ID NO 7
<211> LENGTH: 15
<212> TYPE: PRT
<213> ORGANISM: Artificial Sequence
<220> FEATURE:
<223> OTHER INFORMATION: synthetic

<400> SEQUENCE: 7

Cys Ala Ser Ser Ser Thr Gly Gly Ala Leu Tyr Glu Gln Tyr Phe
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: synthetic

<400> SEQUENCE: 8

Cys Ala Leu Ala Ala Gly Gly Thr Ser Tyr Gly Lys Leu Thr Phe
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: synthetic

<400> SEQUENCE: 9

Cys Ala Ser Ser Gly Ala Tyr Pro Glu Ala Phe Phe
1               5                   10

<210> SEQ ID NO 10
<211> LENGTH: 12
<212> TYPE: PRT
<213> ORGANISM: Artificial Sequence
<220> FEATURE:
<223> OTHER INFORMATION: synthetic

<400> SEQUENCE: 10

Cys Ala Pro Met Asn Arg Asp Asp Lys Ile Ile Phe
1               5                   10

<210> SEQ ID NO 11
<211> LENGTH: 12
<212> TYPE: PRT
<213> ORGANISM: Artificial Sequence
<220> FEATURE:
<223> OTHER INFORMATION: synthetic

<400> SEQUENCE: 11

Cys Ala Ser Ser His Leu Gly Tyr Glu Gln Tyr Phe
1               5                   10
```

-continued

```
<210> SEQ ID NO 12
<211> LENGTH: 13
<212> TYPE: PRT
<213> ORGANISM: Artificial Sequence
<220> FEATURE:
<223> OTHER INFORMATION: synthetic

<400> SEQUENCE: 12

Cys Ala Val Asn Pro Tyr Asn Thr Asp Lys Leu Ile Phe
1               5                   10

<210> SEQ ID NO 13
<211> LENGTH: 13
<212> TYPE: PRT
<213> ORGANISM: Artificial Sequence
<220> FEATURE:
<223> OTHER INFORMATION: synthetic

<400> SEQUENCE: 13

Cys Ser Ala Arg Asp Leu Gly Thr Glu Glu Ala Phe Phe
1               5                   10

<210> SEQ ID NO 14
<211> LENGTH: 16
<212> TYPE: PRT
<213> ORGANISM: Artificial Sequence
<220> FEATURE:
<223> OTHER INFORMATION: synthetic

<400> SEQUENCE: 14

Cys Val Val Ser Leu Arg Ile Thr Gly Gly Gly Asn Lys Leu Thr Phe
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: synthetic

<400> SEQUENCE: 15

Cys Ala Ser Ser Leu Ser Phe Gly Gly Phe Tyr Asn Glu Gln Phe Phe
1               5                   10                  15

<210> SEQ ID NO 16
<211> LENGTH: 12
<212> TYPE: PRT
<213> ORGANISM: Artificial Sequence
<220> FEATURE:
<223> OTHER INFORMATION: synthetic

<400> SEQUENCE: 16

Cys Ala Ser Ser His Leu Gly Tyr Glu Gln Tyr Phe
1               5                   10

<210> SEQ ID NO 17
<211> LENGTH: 14
<212> TYPE: PRT
<213> ORGANISM: Artificial Sequence
<220> FEATURE:
<223> OTHER INFORMATION: synthetic

<400> SEQUENCE: 17

Cys Ala Ala Ser Gly Arg Asn Tyr Gly Gln Asn Phe Val Phe
1               5                   10

<210> SEQ ID NO 18
```

```
<211> LENGTH: 15
<212> TYPE: PRT
<213> ORGANISM: Artificial Sequence
<220> FEATURE:
<223> OTHER INFORMATION: synthetic

<400> SEQUENCE: 18

Cys Leu Arg Gly Cys Arg Met Asp Ser Asn Tyr Gln Leu Ile Trp
1               5                   10                  15

<210> SEQ ID NO 19
<211> LENGTH: 13
<212> TYPE: PRT
<213> ORGANISM: Artificial Sequence
<220> FEATURE:
<223> OTHER INFORMATION: synthetic

<400> SEQUENCE: 19

Cys Ser Gly Ile Gly Val Glu Ser Tyr Glu Gln Tyr Phe
1               5                   10

<210> SEQ ID NO 20
<211> LENGTH: 11
<212> TYPE: PRT
<213> ORGANISM: Artificial Sequence
<220> FEATURE:
<223> OTHER INFORMATION: synthetic

<400> SEQUENCE: 20

Cys Ala Val Ser Ser Ser Asn Asn Leu Phe Phe
1               5                   10

<210> SEQ ID NO 21
<211> LENGTH: 15
<212> TYPE: PRT
<213> ORGANISM: Artificial Sequence
<220> FEATURE:
<223> OTHER INFORMATION: synthetic

<400> SEQUENCE: 21

Cys Ala Ser Ser Ser Leu Thr Gly Ala Gly Asp Thr Ile Tyr Phe
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: synthetic

<400> SEQUENCE: 22

Cys Ala Phe Met Asn His Leu Ser Leu Asn Ala Gly Lys Ser Thr Phe
1               5                   10                  15

<210> SEQ ID NO 23
<211> LENGTH: 12
<212> TYPE: PRT
<213> ORGANISM: Artificial Sequence
<220> FEATURE:
<223> OTHER INFORMATION: synthetic

<400> SEQUENCE: 23

Cys Ala Ser Ser Tyr Gly Ala Tyr Glu Gln Tyr Phe
1               5                   10

<210> SEQ ID NO 24
<211> LENGTH: 15
```

```
<212> TYPE: PRT
<213> ORGANISM: Artificial Sequence
<220> FEATURE:
<223> OTHER INFORMATION: synthetic

<400> SEQUENCE: 24

Cys Ala Met Arg Glu Gly Thr Asp Ser Ser Tyr Lys Leu Ile Phe
1               5                   10                  15

<210> SEQ ID NO 25
<211> LENGTH: 17
<212> TYPE: PRT
<213> ORGANISM: Artificial Sequence
<220> FEATURE:
<223> OTHER INFORMATION: synthetic

<400> SEQUENCE: 25

Cys Ala Ser Ser Asn His Glu Glu Trp Gly Ala Ala Ser Pro Leu His
1               5                   10                  15

Phe

<210> SEQ ID NO 26
<211> LENGTH: 14
<212> TYPE: PRT
<213> ORGANISM: Artificial Sequence
<220> FEATURE:
<223> OTHER INFORMATION: synthetic

<400> SEQUENCE: 26

Cys Ala Leu Ala Thr Gly Gly Gly Ala Asp Gly Leu Thr Phe
1               5                   10

<210> SEQ ID NO 27
<211> LENGTH: 18
<212> TYPE: PRT
<213> ORGANISM: Artificial Sequence
<220> FEATURE:
<223> OTHER INFORMATION: synthetic

<400> SEQUENCE: 27

Cys Ala Ser Ser Leu Glu Pro Gly Thr Asp Leu Leu Gly Tyr Gly Tyr
1               5                   10                  15

Thr Phe

<210> SEQ ID NO 28
<211> LENGTH: 15
<212> TYPE: PRT
<213> ORGANISM: Artificial Sequence
<220> FEATURE:
<223> OTHER INFORMATION: synthetic

<400> SEQUENCE: 28

Cys Ala Val Val Ser Arg Gly Gly Thr Ala Ser Lys Leu Thr Phe
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: synthetic

<400> SEQUENCE: 29

Cys Ala Gly Val Ala Arg Lys Ala Ala Gly Asn Lys Leu Thr Phe
1               5                   10                  15
```

```
<210> SEQ ID NO 30
<211> LENGTH: 16
<212> TYPE: PRT
<213> ORGANISM: Artificial Sequence
<220> FEATURE:
<223> OTHER INFORMATION: synthetic

<400> SEQUENCE: 30

Cys Ala Ser Ser Leu Ser Pro Ser Thr Gly Asn Tyr Gly Tyr Thr Phe
1               5                   10                  15

<210> SEQ ID NO 31
<211> LENGTH: 12
<212> TYPE: PRT
<213> ORGANISM: Artificial Sequence
<220> FEATURE:
<223> OTHER INFORMATION: synthetic

<400> SEQUENCE: 31

Cys Ala Val Pro Thr Gly Phe Gln Lys Leu Val Phe
1               5                   10

<210> SEQ ID NO 32
<211> LENGTH: 14
<212> TYPE: PRT
<213> ORGANISM: Artificial Sequence
<220> FEATURE:
<223> OTHER INFORMATION: synthetic

<400> SEQUENCE: 32

Cys Ala Ser Ser Glu Gly Leu Gly Asn Ser Pro Leu His Phe
1               5                   10

<210> SEQ ID NO 33
<211> LENGTH: 13
<212> TYPE: PRT
<213> ORGANISM: Artificial Sequence
<220> FEATURE:
<223> OTHER INFORMATION: synthetic

<400> SEQUENCE: 33

Cys Ala Val Asn Val Pro Leu Ser Tyr Gln Leu Thr Phe
1               5                   10

<210> SEQ ID NO 34
<211> LENGTH: 15
<212> TYPE: PRT
<213> ORGANISM: Artificial Sequence
<220> FEATURE:
<223> OTHER INFORMATION: synthetic

<400> SEQUENCE: 34

Cys Ala Leu Ser Glu Ala Gly Ala Gly Ser Tyr Gln Leu Thr Phe
1               5                   10                  15

<210> SEQ ID NO 35
<211> LENGTH: 17
<212> TYPE: PRT
<213> ORGANISM: Artificial Sequence
<220> FEATURE:
<223> OTHER INFORMATION: synthetic

<400> SEQUENCE: 35

Cys Ala Ser Ser Gln Glu Pro Val Ala Ser Phe Phe Val Glu Gln Phe
1               5                   10                  15

Phe
```

```
<210> SEQ ID NO 36
<211> LENGTH: 11
<212> TYPE: PRT
<213> ORGANISM: Artificial Sequence
<220> FEATURE:
<223> OTHER INFORMATION: synthetic

<400> SEQUENCE: 36

Cys Ile Thr Ser Gly Thr Tyr Lys Tyr Ile Phe
1               5                   10

<210> SEQ ID NO 37
<211> LENGTH: 17
<212> TYPE: PRT
<213> ORGANISM: Artificial Sequence
<220> FEATURE:
<223> OTHER INFORMATION: synthetic

<400> SEQUENCE: 37

Cys Ala Ser Ser Leu Ser Asp Thr Gly Leu Val Asp Tyr Glu Gln Tyr
1               5                   10                  15

Phe

<210> SEQ ID NO 38
<211> LENGTH: 15
<212> TYPE: PRT
<213> ORGANISM: Artificial Sequence
<220> FEATURE:
<223> OTHER INFORMATION: synthetic

<400> SEQUENCE: 38

Cys Ala Ser Ser Leu Leu Thr Gly Phe Gly Thr Glu Ala Phe Phe
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: synthetic

<400> SEQUENCE: 39

Cys Ala Ser Ser Tyr Gln Thr Gly Ala Ser Tyr Gly Tyr Thr Phe
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: synthetic

<400> SEQUENCE: 40

Cys Ala Glu Asn Ser Pro Asn Asn Ala Gly Asn Met Leu Thr Phe
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: synthetic

<400> SEQUENCE: 41

Cys Ala Ser Ser Tyr Gln Thr Gly Ala Ala Tyr Gly Tyr Thr Phe
```

```
1               5               10              15

<210> SEQ ID NO 42
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: Can be any amino acid

<400> SEQUENCE: 42

Cys Ala Val Thr His Trp Xaa Gly Phe Lys Thr Ile Phe
1               5                   10

<210> SEQ ID NO 43
<211> LENGTH: 9
<212> TYPE: PRT
<213> ORGANISM: Artificial Sequence
<220> FEATURE:
<223> OTHER INFORMATION: synthetic

<400> SEQUENCE: 43

Asn Leu Val Pro Met Val Ala Thr Val
1               5
```